(12) United States Patent
Howell et al.

(10) Patent No.: US 8,202,217 B2
(45) Date of Patent: Jun. 19, 2012

(54) HEALTHCARE BASE

(75) Inventors: Thomas A. Howell, Palo Alto, CA (US);
Angeline Hadiwidjaja, Los Altos, CA (US); Peter P. Tong, Mountain View, CA (US); C. Douglass Thomas, Campbell, CA (US)

(73) Assignee: Ip Venture, Inc., Los Altos, CA (US)

( * ) Notice: Subject to any disclaimer, the term of this patent is extended or adjusted under 35 U.S.C. 154(b) by 339 days.

(21) Appl. No.: 11/451,780

(22) Filed: Jun. 12, 2006

(65) Prior Publication Data

US 2006/0241355 A1 Oct. 26, 2006

Related U.S. Application Data

(60) Provisional application No. 60/689,312, filed on Jun. 10, 2005, provisional application No. 60/732,925, filed on Nov. 2, 2005, provisional application No. 60/785,825, filed on Mar. 24, 2006.

(51) Int. Cl.
*A61B 5/00* (2006.01)
*G07F 11/00* (2006.01)
*B65B 59/00* (2006.01)
*G08B 23/00* (2006.01)

(52) U.S. Cl. .......... 600/300; 221/2; 221/3; 221/15; 340/573.1

(58) Field of Classification Search .......... 600/300–301; 128/903–905, 920–921; 340/539, 573.1–576; 705/2–4
See application file for complete search history.

(56) References Cited

U.S. PATENT DOCUMENTS

| 3,214,278 | A | | 10/1965 | Mylo |
| 4,626,105 | A | * | 12/1986 | Miller ............................. 368/10 |
| 4,835,372 | A | | 5/1989 | Gombrich et al. |
| 4,883,063 | A | | 11/1989 | Bernard et al. |
| 4,931,046 | A | | 6/1990 | Newman |
| 4,966,152 | A | | 10/1990 | Gäng et al. |
| 5,014,798 | A | | 5/1991 | Glynn |
| 5,142,484 | A | * | 8/1992 | Kaufman et al. ............. 600/300 |

(Continued)

FOREIGN PATENT DOCUMENTS

EP 0 274 363 B1 7/1988

(Continued)

OTHER PUBLICATIONS

"High-tech revolutionizes home health care", Health Day, Azcentral.com, Jan. 21, 2005, pp. 1-2.

(Continued)

*Primary Examiner* — Sam Yao
*Assistant Examiner* — Shirley Jian

(57) ABSTRACT

One embodiment includes a healthcare base for the health of a user. The base includes an area to receive a bottle that carries a health-related substance for the user to take. The base includes a detector, an input mechanism, an output mechanism and a storage medium. The detector can electronically detect information from the bottle. The input mechanism can allow the user to input information into the base. The output device can allow the user to receive output from the base. The storage medium can electrically store a piece of information regarding the user. In addition to electronically detect information from the bottle, the base provides electronic assistance regarding taking the health-related substance. In another embodiment, the base includes a space to receive a sensor. The sensor can measure an attribute of the user with the health-realted substance affecting the results of the measurements.

23 Claims, 31 Drawing Sheets

U.S. PATENT DOCUMENTS

| | | | |
|---|---|---|---|
| 5,353,802 A | 10/1994 | Ollmar | |
| 5,394,206 A | 2/1995 | Cocca | |
| 5,471,382 A | 11/1995 | Tallman et al. | |
| 5,495,961 A | 3/1996 | Maestre | |
| 5,617,812 A | 4/1997 | Balderson et al. | |
| 5,633,910 A | 5/1997 | Cohen | |
| 5,642,731 A | 7/1997 | Kehr | |
| 5,673,692 A | 10/1997 | Schulze et al. | |
| 5,724,580 A | 3/1998 | Levin et al. | |
| 5,737,539 A | 4/1998 | Edelson et al. | |
| 5,823,948 A | 10/1998 | Ross, Jr. et al. | |
| 5,833,625 A | 11/1998 | Essen-Moller | |
| 5,845,255 A | 12/1998 | Mayaud | |
| 5,875,108 A | 2/1999 | Hoffberg et al. | |
| 5,913,834 A | 6/1999 | Francais | |
| 5,928,168 A | 7/1999 | Laros, Jr. | |
| 5,938,593 A | 8/1999 | Ouellette | |
| 6,014,630 A | 1/2000 | Jeacock et al. | |
| 6,032,119 A | 2/2000 | Brown et al. | |
| 6,039,688 A | 3/2000 | Douglas et al. | |
| 6,139,494 A | 10/2000 | Cairnes | |
| 6,151,586 A * | 11/2000 | Brown | 705/14.19 |
| 6,169,707 B1 * | 1/2001 | Newland | 368/10 |
| 6,187,291 B1 | 2/2001 | Weinstein et al. | |
| 6,248,067 B1 | 6/2001 | Causey, III et al. | |
| 6,259,654 B1 * | 7/2001 | de la Huerga | 368/10 |
| 6,277,071 B1 | 8/2001 | Hennessy et al. | |
| 6,294,999 B1 * | 9/2001 | Yarin et al. | 340/573.1 |
| 6,302,844 B1 | 10/2001 | Walker et al. | |
| 6,319,199 B1 | 11/2001 | Sheehan et al. | |
| 6,324,123 B1 * | 11/2001 | Durso | 368/10 |
| 6,370,426 B1 | 4/2002 | Campbell et al. | |
| 6,375,469 B1 | 4/2002 | Brown | |
| 6,443,890 B1 | 9/2002 | Schulze et al. | |
| 6,454,705 B1 | 9/2002 | Cosentino et al. | |
| 6,485,982 B1 | 11/2002 | Charlton | |
| 6,529,446 B1 * | 3/2003 | de la Huerga | 368/10 |
| 6,529,767 B1 | 3/2003 | Woo et al. | |
| 6,569,094 B2 | 5/2003 | Suzuki et al. | |
| 6,602,469 B1 | 8/2003 | Maus et al. | |
| 6,604,650 B2 | 8/2003 | Sagar | |
| 6,610,012 B2 | 8/2003 | Mault | |
| 6,612,984 B1 | 9/2003 | Kerr, II | |
| 6,640,212 B1 | 10/2003 | Rosse | |
| 6,698,590 B2 | 3/2004 | Moore | |
| 6,736,759 B1 | 5/2004 | Stubbs et al. | |
| 6,789,936 B1 | 9/2004 | Kraus et al. | |
| 6,847,892 B2 | 1/2005 | Zhou et al. | |
| 6,942,616 B2 | 9/2005 | Kerr, II | |
| 6,957,777 B1 | 10/2005 | Huang | |
| 7,158,011 B2 * | 1/2007 | Brue | 340/309.16 |
| 7,170,823 B2 * | 1/2007 | Fabricius et al. | 368/10 |
| 7,304,582 B2 * | 12/2007 | Kerr et al. | 340/573.4 |
| 7,330,101 B2 * | 2/2008 | Sekura | 340/309.4 |
| 7,369,919 B2 * | 5/2008 | Vonk et al. | 700/236 |
| 7,402,135 B2 | 7/2008 | Leveque et al. | |
| 2001/0013006 A1 | 8/2001 | Brown | |
| 2001/0034615 A1 | 10/2001 | Wilkinson et al. | |
| 2001/0037215 A1 | 11/2001 | Sparks | |
| 2001/0039504 A1 | 11/2001 | Linberg et al. | |
| 2002/0010597 A1 | 1/2002 | Mayer et al. | |
| 2002/0017996 A1 * | 2/2002 | Niemiec | 340/573.1 |
| 2002/0022973 A1 | 2/2002 | Sun et al. | |
| 2002/0026105 A1 | 2/2002 | Drazen | |
| 2002/0035316 A1 | 3/2002 | Drazen | |
| 2002/0038227 A1 | 3/2002 | Fey et al. | |
| 2002/0040282 A1 | 4/2002 | Bailey et al. | |
| 2002/0042725 A1 | 4/2002 | Mayaud | |
| 2002/0042726 A1 | 4/2002 | Mayaud | |
| 2002/0049615 A1 | 4/2002 | Huber | |
| 2002/0052761 A1 | 5/2002 | Fey et al. | |
| 2002/0062225 A1 | 5/2002 | Siperco | |
| 2002/0062230 A1 | 5/2002 | Morag et al. | |
| 2002/0072933 A1 | 6/2002 | Vonk et al. | |
| 2002/0072934 A1 | 6/2002 | Ross et al. | |
| 2002/0077849 A1 | 6/2002 | Baruch et al. | |
| 2002/0082480 A1 | 6/2002 | Riff et al. | |
| 2002/0082865 A1 | 6/2002 | Bianco et al. | |
| 2002/0087361 A1 | 7/2002 | Benigno et al. | |
| 2002/0104848 A1 | 8/2002 | Burrows et al. | |
| 2002/0111559 A1 | 8/2002 | Kurata et al. | |
| 2002/0120471 A1 | 8/2002 | Drazen | |
| 2002/0147617 A1 | 10/2002 | Schoenbaum et al. | |
| 2002/0198473 A1 | 12/2002 | Kumar et al. | |
| 2003/0017440 A1 | 1/2003 | Bergey et al. | |
| 2003/0023461 A1 | 1/2003 | Quintanilla et al. | |
| 2003/0036683 A1 | 2/2003 | Kehr et al. | |
| 2003/0050731 A1 | 3/2003 | Rosenblum | |
| 2003/0055679 A1 | 3/2003 | Soll et al. | |
| 2003/0062046 A1 | 4/2003 | Wiesmann et al. | |
| 2003/0182162 A1 | 9/2003 | Stevens | |
| 2003/0204359 A1 * | 10/2003 | Blakley | 702/130 |
| 2003/0208108 A1 | 11/2003 | Shewmake et al. | |
| 2003/0211007 A1 | 11/2003 | Maus et al. | |
| 2004/0034284 A1 | 2/2004 | Aversano et al. | |
| 2004/0034288 A1 | 2/2004 | Hennesy et al. | |
| 2004/0037738 A1 | 2/2004 | Maus et al. | |
| 2004/0038389 A1 | 2/2004 | Maus et al. | |
| 2004/0039255 A1 | 2/2004 | Simonsen et al. | |
| 2004/0044546 A1 | 3/2004 | Moore | |
| 2004/0049355 A1 | 3/2004 | Maus et al. | |
| 2004/0078211 A1 | 4/2004 | Schramm-Apple et al. | |
| 2004/0078220 A1 | 4/2004 | Jackson | |
| 2004/0078231 A1 | 4/2004 | Wilkes et al. | |
| 2004/0122706 A1 | 6/2004 | Walker et al. | |
| 2004/0139048 A1 | 7/2004 | Kerr et al. | |
| 2004/0204959 A1 | 10/2004 | Moreano et al. | |
| 2004/0215369 A1 | 10/2004 | Rosenblum | |
| 2004/0236944 A1 | 11/2004 | Walker et al. | |
| 2004/0245205 A1 | 12/2004 | Egli et al. | |
| 2004/0249672 A1 | 12/2004 | Bocionek et al. | |
| 2004/0260155 A1 | 12/2004 | Ciarniello et al. | |
| 2004/0264300 A1 | 12/2004 | Gratkowski | |
| 2005/0021370 A1 | 1/2005 | Riff et al. | |
| 2005/0022817 A1 | 2/2005 | Alvey | |
| 2005/0027562 A1 | 2/2005 | Brown | |
| 2005/0033369 A1 | 2/2005 | Badelt | |
| 2005/0143675 A1 | 6/2005 | Neel et al. | |
| 2005/0267377 A1 | 12/2005 | Marossero et al. | |
| 2006/0231109 A1 | 10/2006 | Howell et al. | |
| 2006/0248946 A1 | 11/2006 | Howell et al. | |
| 2007/0024465 A1 | 2/2007 | Howell et al. | |
| 2007/0048224 A1 | 3/2007 | Howell et al. | |
| 2007/0213606 A1 | 9/2007 | Sherman et al. | |
| 2007/0225578 A1 | 9/2007 | Howell et al. | |
| 2008/0068559 A1 | 3/2008 | Howell et al. | |
| 2008/0146890 A1 | 6/2008 | LeBoeuf et al. | |
| 2008/0183287 A1 | 7/2008 | Ayre | |

FOREIGN PATENT DOCUMENTS

| | | |
|---|---|---|
| EP | 1 184 663 A2 | 3/2002 |

OTHER PUBLICATIONS

"Sensing device that when implanted in the mouth can detect hydration levels in soldiers", News-Medical.net . . . , Devices/Technology, May 18, 2004, 3 pages.

"When you want the very best . . . e-pill MD.2 Monitored Automatic Pill Dispenser", http://www.epill.com/howmd2works.html, downloaded Nov. 9, 2005, pp. 1-2.

Choi, Candice, "Virtual Medical Checkups on the Rise," ABC News, 2006, http://abcnews.go.com/Health/print?id=1715941, downloaded Mar. 15, 2006.

Marketing Devices, http://www.courage-khazaka.de/products/marketing_products.htm, downloaded May 14, 2007, pp. 1-4.

Products for Dermatology, http://www.courage-khazaka.de/products/derma_products.htm, downloaded May 14, 2007, pp. 1-4.

Scientific Devices, http://www.courage-khazaka.de/products/scientific_rd_prod.htm, downloaded May 14, 2007, pp. 1-5.

e-pill Pill Bottle Multi Alarm, http://www.epill.com/bottle.html, downloaded Dec. 5, 2006.

étude, The Way to skin counseling, Operation Manual, front cover page and pp. 1-27.

FitSense Technology, Inc., FS-1 Frequently Asked Questions, http://www.fitsense.com/FS1FAQ.aspx, downloaded Apr. 23, 2006, 2 pages.

FitSense Technology, Inc., FS-1 Speedometer, Athlete's Manual, version 2.0 Jul. 2, 2001, 32 pages.
FitSense Technology, Inc., ActiHealth Intelligent Health Network, downloaded Apr. 23, 2006, 1 page.
FitSense Technology, Inc., ActiHealth Personal Monitoring System, http://www.fitsense.com/SystemDevice.aspx, downloaded Apr. 23, 2006, 2 pages.
FitSense Technology, Inc., BodyLan, Ultra Low-Power Wireless Personal Area Network, http://www.fitsense.com/Wireless.aspx, downloaded Apr. 23, 2006, 1 page.
FitSense Technology, Inc., FitSense FS-1 Speedometer, http://www.fitsense.com/FS1.aspx, downloaded Apr. 23, 2006, 2 pages.
FitSense Technology, Inc., Health & Wellness Program Providers, Personalized monitoring & feedback tools, http://www.fitsense.com/HealthWellness.aspx, downloaded Apr. 23, 2006, 1 page.
FitSense Technology, Inc., Health Coaches & Disease Management Providers, Personalized monitoring & feedback tools, http://www.fitsense.com/DiseaseManagement.aspx, downloaded Apr. 23, 2006, 1 page.
Freudenrich, Craig, "How Prenatal Testing Works", HowStuffWorks, Inc., downloaded Mar. 23, 2007, pp. 1-11.
GOJO Skin Care Lab, Fast, Effective Hand Cleaning, downloaded Nov. 29, 2006, pp. 1-2.
L'Oréal and STMicroelectronics applying semiconductors to skin aging, Press Release, Geneva, Oct. 18, 2002, pp. 2.
LifePoint Inc.—Saliva Based Testing Systems for the next generation, LifePoint® IMPACT® Test System, undated, 2 pages.
Mirkin, Gabe M.D., "Recovery Pulse Rate: Heart Attack?," http://www.drmirkin.com/heart/8076.html, Oct. 28, 1999, 1 page.
Moritex USA Incorporated, Sensors & Meters, copyright 2004, http://www.moritexusa.com/products/product_category.php-?plid=5&pcid=10, downloaded Apr. 19, 2006, pp. 1-2.
Nellcor OxiMax, Sensor Selection Guide, Tyco Healthcare, Oct. 2002, 12 pages.
NELLCOR™ Oximax Sensors™, Tyco Healthcare Group, 2002, pp. 1-5.
"NOVA Technology Beams Up the Petite," ATSP Online, http://www.atsp.org/news/supplier.asp?contentID=863&FullStory=, 2007, p. 1-6.
Our Solutions, Carematix Wellness System, Carematix Inc., 2002, 1 page.
Physician Office Products, Chemstrip® Micral® Test Strips, Roche Diagnostics, 2004, 2 pages.
Physician Office Products, Chemstrip® Urine Test Strips, Roche Diagnostics, 2004, 3 pages.
RemindHer, NVOrganon, http://www.contraception.net, 2004, pp. 1-2.
Skin Care and Aging, U.S. National Institutes of Health, National Institute on Aging, last updated Dec. 29, 2005, pp. 1-7.
Wireless Assistant for Physicians and Relatives of Hospitalized Patients, UCLA Technology Available for Licensing, http://www.research ucla.edu/tech, Publ. No. US-2004-0073453-A1, 2001, 4 pages.
U.S. Appl. No. 10/397,641, filed Mar. 26, 2003.
U.S. Appl. No. 11/314,545, filed Dec. 20, 2005.
U.S. Appl. No. 11/451,781, filed Jun. 12, 2006.
U.S. Appl. No. 11/479,665, filed Jun. 30, 2006.
U.S. Appl. No. 11/491,774, filed Jul. 22, 2006.
U.S. Appl. No. 11/592,431, filed Nov. 2, 2006.
U.S. Appl. No. 11/888,723, filed Sep. 2, 2007.
U.S. Appl. No. 11/821,150, filed Jun. 22, 2007.
U.S. Appl. No. 11/725,360, filed Mar. 17, 2007.

* cited by examiner

935

Address User —937

↓

Monitor User Blood Pressure —939

↓

Are Measurements Beyond Thresholds —— Yes —→ Provide Alert —941

↓ No

Provide User with Visual Report —943

977　Asks User Guardian
Questions

Recommends
Dosage to Parent   979

Alert Doctor if Drug
Abuse   981

HEALTHCARE BASE

CROSS-REFERENCE TO RELATED APPLICATIONS

This application is related to U.S. patent application Ser. No. 11/314,545, filed Dec. 20, 2005, and entitled "BOTTLE OF LOTION WITH A SENSOR," which is hereby incorporated herein by reference, which claims priority to each of: (i) U.S. Provisional Patent Application No. 60/636,969, filed Dec. 20, 2004, entitled "PREVENTIVE MEDICAL SYSTEMS, METHODS AND APPARATUS," and which is hereby incorporated herein by reference; (ii) U.S. Provisional Patent Application No. 60/652,213, filed Feb. 14, 2005, entitled "PREVENTIVE MEDICAL SYSTEMS, METHODS AND APPARATUS," and which is hereby incorporated herein by reference; (ill) U.S. Provisional Patent Application No. 60/670,957, filed Apr. 13, 2005, entitled "BOTTLE OF LOTION WITH A LOTION SENSOR," and which is hereby incorporated herein by reference; (iv) U.S. Provisional Patent Application No. 60/689,312, filed Jun. 10, 2005, entitled "PERSONAL AND PORTABLE BOTTLE," and which is hereby incorporated herein by reference; and (v) U.S. Provisional Patent Application No. 60/732,925, filed Nov. 2, 2005, entitled "METHOD AND APPARATUS TO SENSE HYDRATION LEVEL OF A PERSON," and which is hereby incorporated herein by reference.

This application also claims priority to: (i) U.S. Provisional Patent Application No. 60/689,312, filed Jun. 10, 2005, entitled "PERSONAL AND PORTABLE BOTTLE," and which is hereby incorporated herein by reference; (ii) U.S. Provisional Patent Application No. 60/732,925, filed Nov. 2, 2005, entitled "METHOD AND APPARATUS TO SENSE HYDRATION LEVEL OF A PERSON," and which is hereby incorporated herein by reference; and (iii) U.S. Provisional Patent Application No. 60/785,825, filed Mar. 24, 2006, entitled "MEDICAL MONITORING SYSTEM," and which is hereby incorporated herein by reference.

BACKGROUND OF THE INVENTION

When a person does not feel well, typically he would take some medication. If he is young and is in relatively good health, he would get well after some time. On the other hand, if he is old and has been taking other types of medication, he has to be careful. There could be complications due to the interactions of the different types of medication he has been taking.

If complications do occur, usually he would go to see a doctor, who would ask him questions to try to find out what has happened. It is not uncommon for a patient to give the doctor some vague answers, such as, "I don't feel well", or "The pain is killing me." He is not being evasive. He really does not feel well. It may simply be difficult for him to clearly remember in details what has happened.

Such problems are not uncommon, particularly for the older generation. Some of them could not even remember what they ate for breakfast 30 minutes ago. It is unreasonable to expect them to accurately tell the doctor the history of their conditions.

Thus, it is not uncommon for a daughter to worry about her mother and call her a number of times every day just to be sure that she has been taking her medication correctly. Both sides could be frustrated by the calls. The mother might find her daughter too pushy, while the daughter might find her mother too incompetent, while feeling guilty about her feeling.

It should be apparent from the foregoing that there is still a need to inexpensively manage the taking of healthcare products. Such needs would increase due to the aging of the population.

SUMMARY OF THE INVENTION

A number of embodiments of the invention generally pertain to a healthcare base or use thereof. The base is for the health of one or more people, and is applicable to different locations, such as for home use, or for use in a nursing home or medical clinic. In one embodiment, the base includes an area to receive a bottle that carries a health-related substance for a user to take. The health-related substance can be a type of medication. The base also includes a detector, an input mechanism, an output mechanism and a storage medium. The detector can electronically detect information from the bottle. As an example, the detector is a barcode reader. The input mechanism can allow the user to input information into the base. The output device can allow the user to receive output from the base. The storage medium can electrically store a piece of information regarding the user. In addition to electronically detecting information from the bottle, the base provides electronic assistance regarding taking the health-related substance. For example, with the base, when a portion of the health-related substance is removed from the bottle, the base keeps track of it.

If the user takes more than one type of medication, and they are in different bottles, in one embodiment, the base automatically look for conflicts among or between the different types of medication. If there are problems, the base could alert the user.

In another embodiment, the base includes a space to receive a sensor. The sensor can measure an attribute of the user with the health-related substance in a bottle affecting the results of the measurements. For example, the sensor is a thermometer, and the health-related substance in a bottle received by the base is Aspirin. With the base, each time when the user takes a measurement with the sensor, the base keeps track of the measurement and the time of the measurement.

In one embodiment, the input mechanism in the base could receive a voice message from the user, and the message can be time-stamped. For example, the user does not feel well. The user could digitally record how he feels in the base. Later when he goes to see a health-care provider, he could download one or more messages he previously recorded into a memory stick or a small memory device for the provider to review.

In one embodiment, information in the base could be wirelessly transmitted to a person or entity interested in the well-being of the user. For example, information regarding the user taking medication from a bottle is automatically sent to the user's daughter after each consumption.

In one embodiment, the base is connected to a health-related device, such as an exercise machine. From the user's information stored in the base, the base could guide the user through an exercise routine. The routine could be linked to a weight-loss program.

In another embodiment, the base could provide motivation for the user to take a health-related substance in a bottle. For example, information in a base could be sent to an insurance company, which determines if incentives should be provided to the user. One incentive could be reducing the premium the user has to pay for his healthcare insurance.

Other aspects and advantages of the present invention will become apparent from the following detailed description, which, when taken in conjunction with the accompanying drawings, illustrates by way of example the principles of the invention.

BRIEF DESCRIPTION OF THE DRAWINGS

FIGS. 16A-16D show examples of different applications of the present invention for prescription drugs according to different embodiments of the invention.

Same numerals in FIGS. 1-17 are assigned to similar elements in all the figures. Embodiments of the invention are discussed below with reference to FIGS. 1-17. However, those skilled in the art will readily appreciate that the detailed description given herein with respect to these figures is for explanatory purposes as the invention extends beyond these limited embodiments.

DETAILED DESCRIPTION OF THE INVENTION

Figure 1:
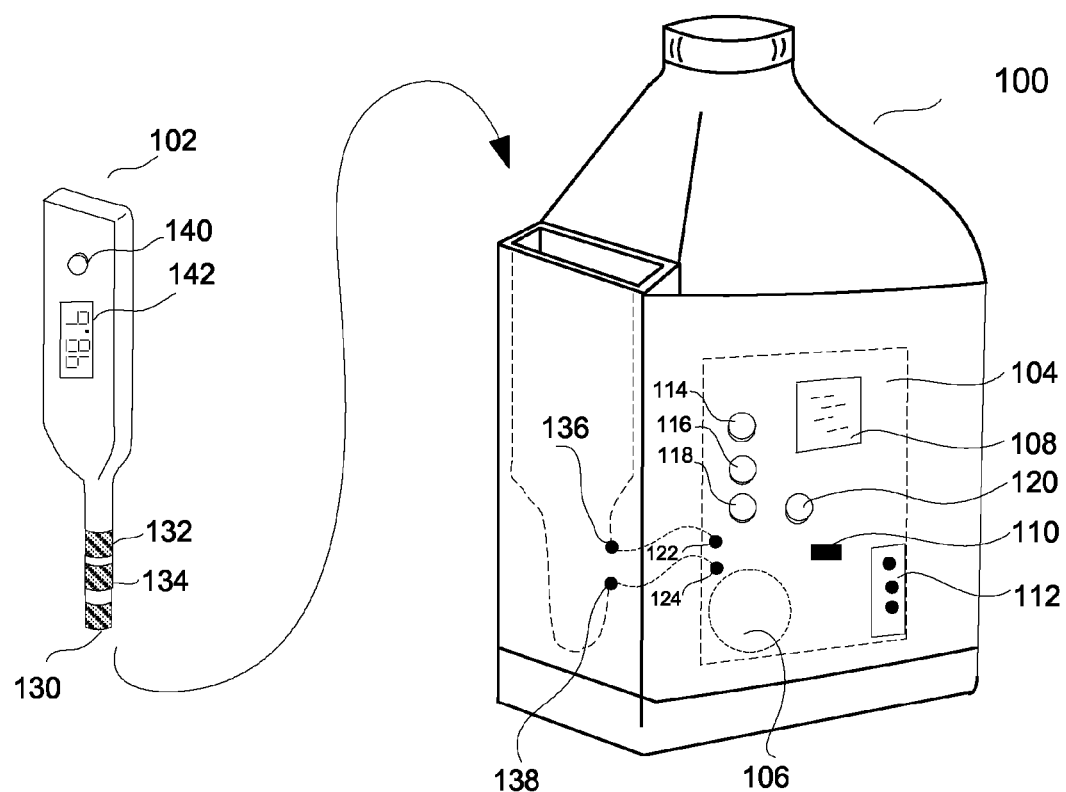
FIG. 1 shows a bottle with a thermometer according to one embodiment of the invention.

FIG. 1 shows a portable bottle 100 with a thermometer 102 according to one embodiment. The bottle 100 can keep personal information of a user, and the information can be from a sensor integral with or coupled to the bottle 100. In this embodiment, the sensor is a thermometer 102 that can measure the temperatures of the user, and the bottle 100 can carry Acetaminophen pills.

Figure 2:
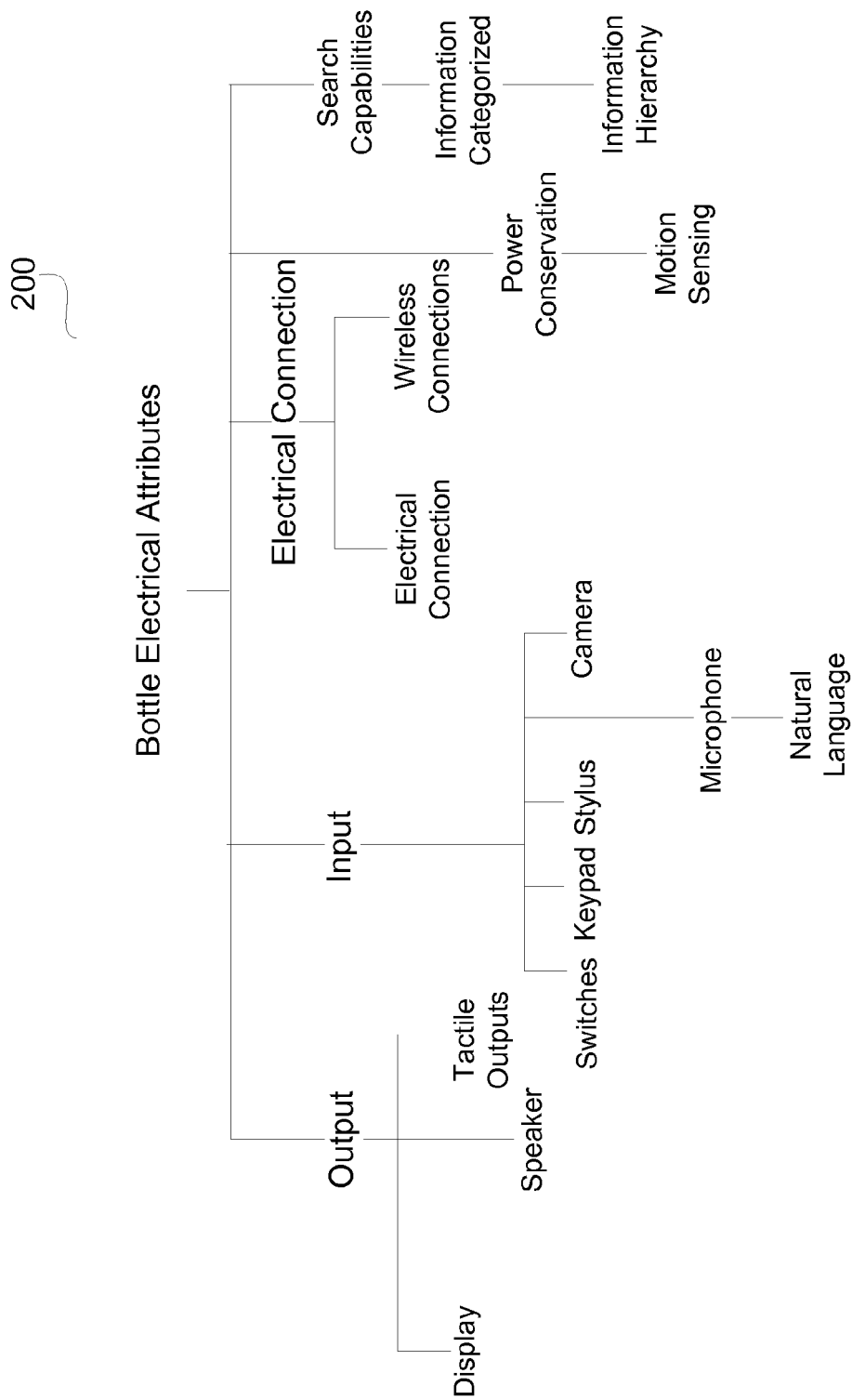
FIG. 2 shows examples of a bottle's electrical attributes according to different embodiments of the invention.

FIG. 2 shows examples of a bottle's electrical attributes 200 according to different embodiments. The bottle can have one or more output mechanisms. For example, the bottle can have a display. The display can be a liquid crystal display. In one embodiment, the display is an electrophoretic display. The bottle can have a speaker to provide audio outputs. The audio signals can be a song, or a part of a song, such as a ring tone. In another embodiment, the output is a form of tactile output, or the output can depend on vibrations.

In one embodiment, the bottle can have one or more input mechanisms. The bottle can have one or more input buttons or switches, a keypad and/or stylus to allow inputs by hand. There can be a pull-down menu on a display on the bottle. The stylus can activate the pull-down menu to enter information into the bottle. The inputs can be through voice. There can be a microphone on the bottle to receive voice signals by the user. The bottle can understand natural language by the user. There are different approaches to implement such natural-language comprehension, as discussed, for example, in U.S. Pat. No. 6,498,921, entitled, "Method and system to answer a natural-language question", which is hereby incorporated by reference into this application. In yet another embodiment, the input mechanism is visual. The bottle can include a camera to take pictures as entry.

In one embodiment, the bottle includes one or more electrical connection mechanisms to couple the bottle to one or more electrical devices. One such electrical connection mechanism is an electrical connector, which can be used to plug the bottle to a physical network. For example, the bottle can have a standard electrical connector, such as a USB connector. As another example, the bottle has a non-standard electrical connector. Such connector can connect the bottle to another electrical device, such as a memory device, like a flash card, or connect the bottle to a computer.

Figure 3:
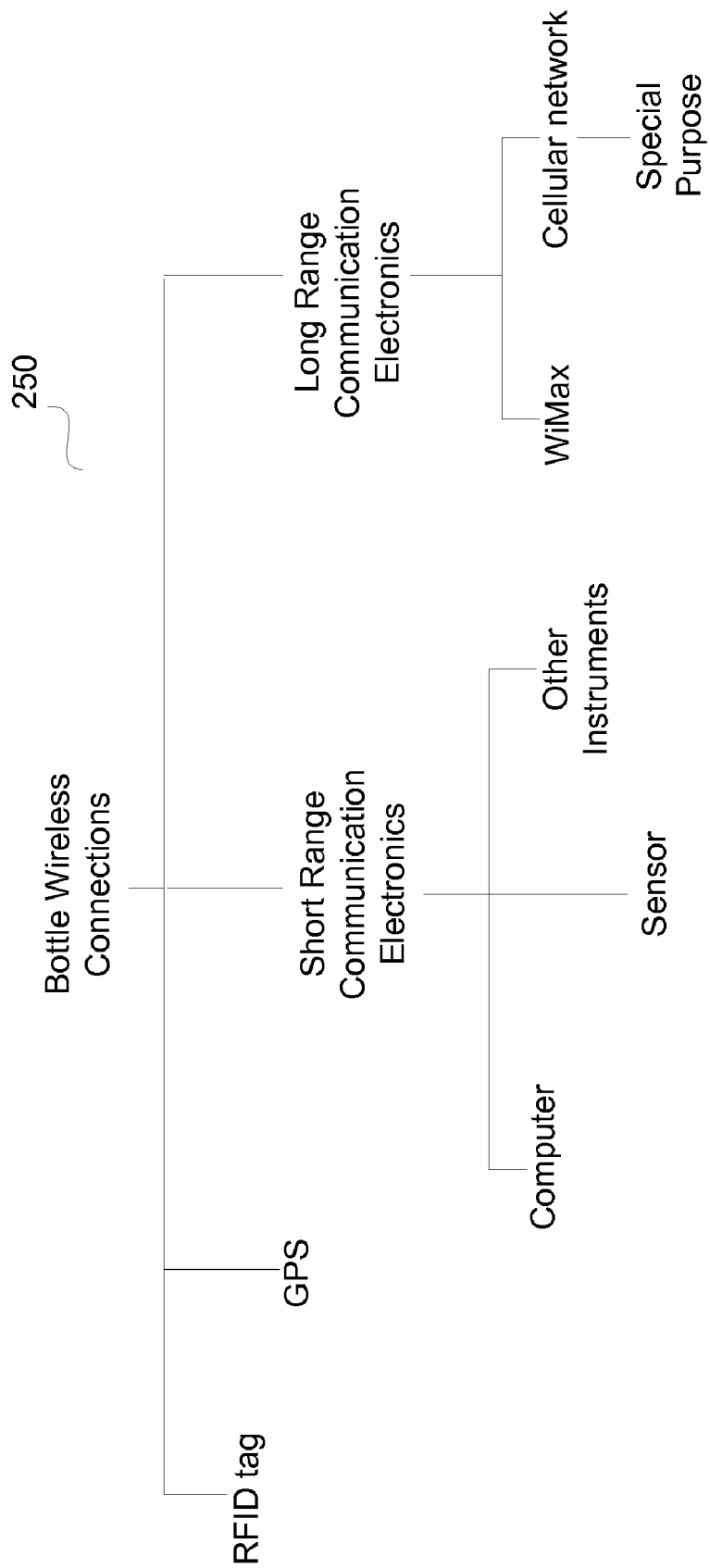
FIG. 3 shows examples of a bottle's wireless connections according to different embodiments of the invention.

In one embodiment, the bottle can include electronic circuits to allow the bottle to be coupled to a wireless network. FIG. 3 shows examples of a bottle's wireless connections 250 according to different embodiments. For example, the bottle has a RFID tag to allow the bottle to be coupled to a RFID network. RFID tags typically include memory chips equipped with radio antennas. Typically, the memory chips do not include tremendous amount of information. They may only have 2 kilobytes, sufficient to encode, such as a serial number, where and when a product was manufactured, and other relevant information. These tags can come in a number of configurations. For example, an active tag uses a battery-powered transponder to emit a constant signal carrying the identifying information programmed into the chip. Active tags are more applicable to situations where readers are not close to the tags. A semi-passive tag likewise has a battery, but may not be activated until it receives a signal from a reader. They are more applicable to situations that do not need continuous connection and accessing. A passive tag has no battery; its antenna extracts power from the reader's radio wave signal to transmit the identifying information on the chip. Passive tags are typically relatively inexpensive, but may have to be within a few feet of a reader to extract power.

In another embodiment, the bottle includes a position-sensing device, which can be based on GPS technologies, to couple to position-sensing information. For example, the device can wirelessly acquire position signals, extract raw position data from the signals, and convert the raw position data into the position of the position-sensing device.

In one embodiment, the bottle includes electronics for short-range communications, such as those based on Bluetooth, UWB, Zigbee, WiFi, infrared or other types of short-distance wireless transmission standards. For example, the bottle can include a short-range analog or digital wireless transceiver under one of the standards. Based on the short-range communication electronics, the bottle can wirelessly connect to another computing device, another sensing device and/or another instrument.

In another embodiment, the bottle includes electronics for long-range or longer-range communications, such as those based on WiMax or cell-phone standards. For example, the bottle can include a special purpose one-way phone that is only connected to one or more specific destinations. For example, instead of dialing all the numbers of the destination(s), a person only needs to push one button on the bottle, and the bottle will be connected to the destination(s). One such location can be the cell phone number of a healthcare provider of the user. Another can be a SMS message to an electronic address of a relative of the user. Yet another can be to a 911 operator.

Based on one or more electrical connections, information in a bottle can be transferred to another device, or bottle. For example, information in a bottle can be downloaded to a storage medium. In another example, information in a bottle can be transferred to another bottle.

In one embodiment, a bottle can be battery powered. The battery can be re-chargeable. In another example, the battery is not designed to be replaceable by the user. In another embodiment, a bottle includes power conservation algorithm. For example, the bottle goes into a sleep mode if its electronics are not activated or if there is no input into the bottle for more than a pre-set period of time, such as fifteen minutes. In another example, to conserver power, the display on the bottle is turned on only if a motion sensor in the bottle senses motion in the immediate vicinity of the bottle, or if the bottle has been moved.

In another embodiment, the bottle includes browse/search capabilities to allow information in the bottle to be browsed/searched and accessed. For example, different pieces of information stored in an electronic storage device in a bottle can be categorized, and the categorization can be hierarchical, with multiple levels in the hierarchy. To illustrate, assume that there are two levels. The top level can be the name of a medication, and the second level can be the time a specific medication was taken. The entries, such as the name of a medication, can be abbreviated. There can be a control knob or switch to allow the user to scroll down entries in a level. By pushing the knob, the user selects an entry, which can lead the user to the next level. There can be an entry for moving up a level also. In one embodiment, once an entry is selected, the identity of that entry will be announced. For example, a selected entry is about acetaminophen or Aspirin. Once that entry is selected, a speaker in the bottle will announce, "Aspirin." If that is the one the user wants, the user can signal his preference by, for example, pushing a switch in the bottle. Another example of information access is through, for example, pull-down menus, as discussed, for example, in U.S. Pat. No. 6,839,699, "Natural query interface based on concept selection," which is hereby incorporated by reference.

In the example shown in FIG. 1, a plurality of the bottle's electrical components can be on a printed circuit board 104. To clarify the description, the figure only shows some of the components, such as a printed circuit board 104 with four input buttons, a battery 106, a LCD display 108, a microcontroller unit 110 and an output port 112 with three connecting contacts. The four input buttons 114, 116, 118 and 120, can be for up, down, back and enter (or select) respectively. The up button 114 can be used to move a curser on the display 108 up, the down button 116 move the curser down, the back button 118 allow the user to go back to the previous entry, and the enter button 120 allow the user to select an entry.

In one embodiment, any of the buttons can serve as an on switch for the bottle. If any of the buttons is pushed, the bottle will be activated. If no buttons are pushed, or no entries are made for a duration of time, such as 10 minutes, the bottle will deactivate. In another embodiment, after activation, the display 108 can show an exit icon, which, if entered, will turn off the bottle.

The three contacts of the output port 112 can be for Tx, Rx and Gnd connections respectively. In another embodiment, the output port can be a standard connector, like a telephone plug.

In the example shown in FIG. 1, the printed circuit board 104 also includes two electrical connecting points 122 and 124 to receive two leads from signals from the sensor 102. In one embodiment, the temperature sensor 102 includes a heat sensor 130, such as a thermocouple, located at the tip of the temperature sensor 102. The temperature sensor 102 also includes two conductors, 132 and 134, configured to connect to two conductors, 136 and 138, at the bottle 100 (for example, when the sensor 102 is placed into a slot or opening of the bottle, such as shown in FIG. 1) to upload information, such as temperature information, from the sensor 102 to the bottle 100. Instead of physical connections, in one embodiment, the connections between the bottle 100 and the temperature sensor 102 can be wireless connections.

The temperature sensor 102 also can include an on/off switch 140 and a display 142, such as a LCD display, to show temperatures measured.

Figure 4A:
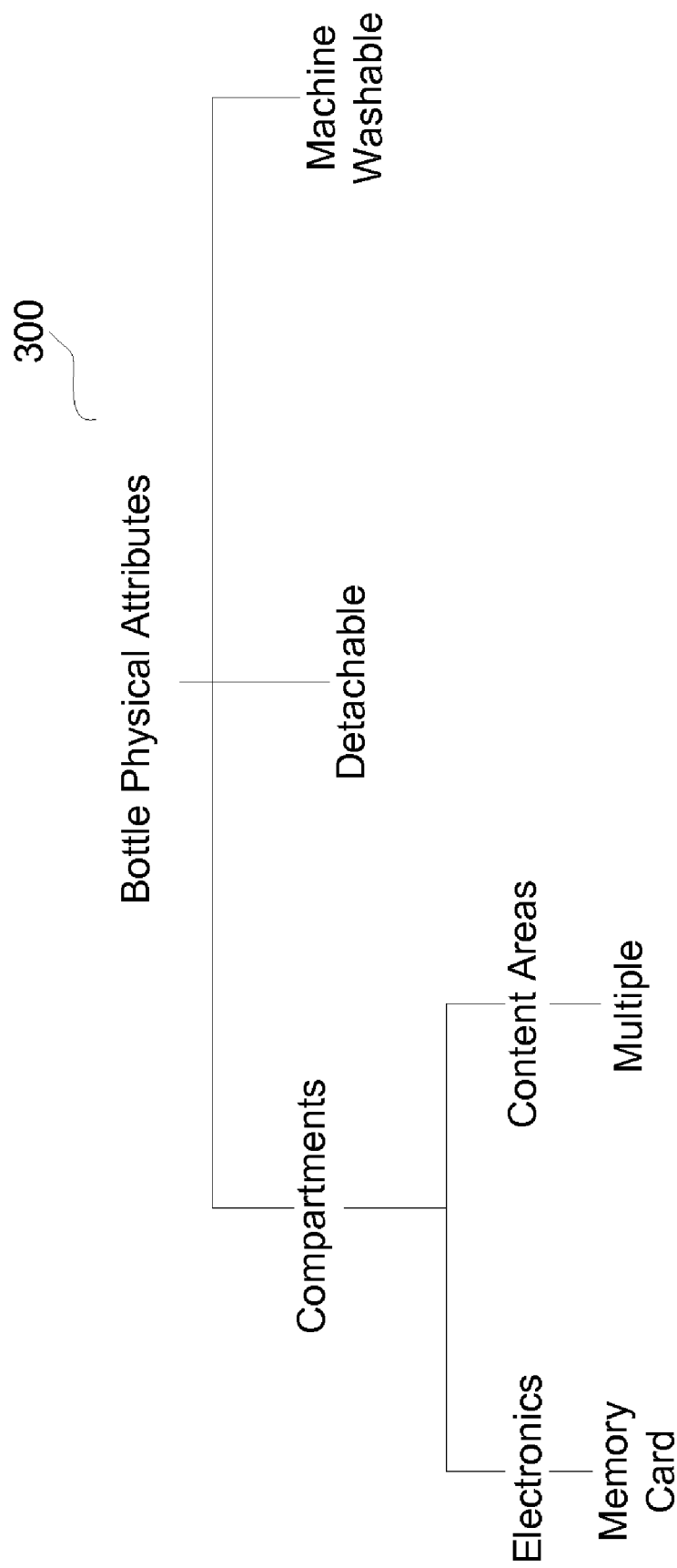
FIG. 4A shows examples of a bottle's physical attributes according to different embodiments of the invention.

FIG. 4A shows examples of a bottle's physical attributes 300 according to different embodiments. In one embodiment, the bottle includes multiple compartments. One compartment can be for all or most of the electrical components in the bottle. In one embodiment, the electrical components can include a memory card or a memory stick that is removable. Information can be stored in the memory card.

Figure 4B:
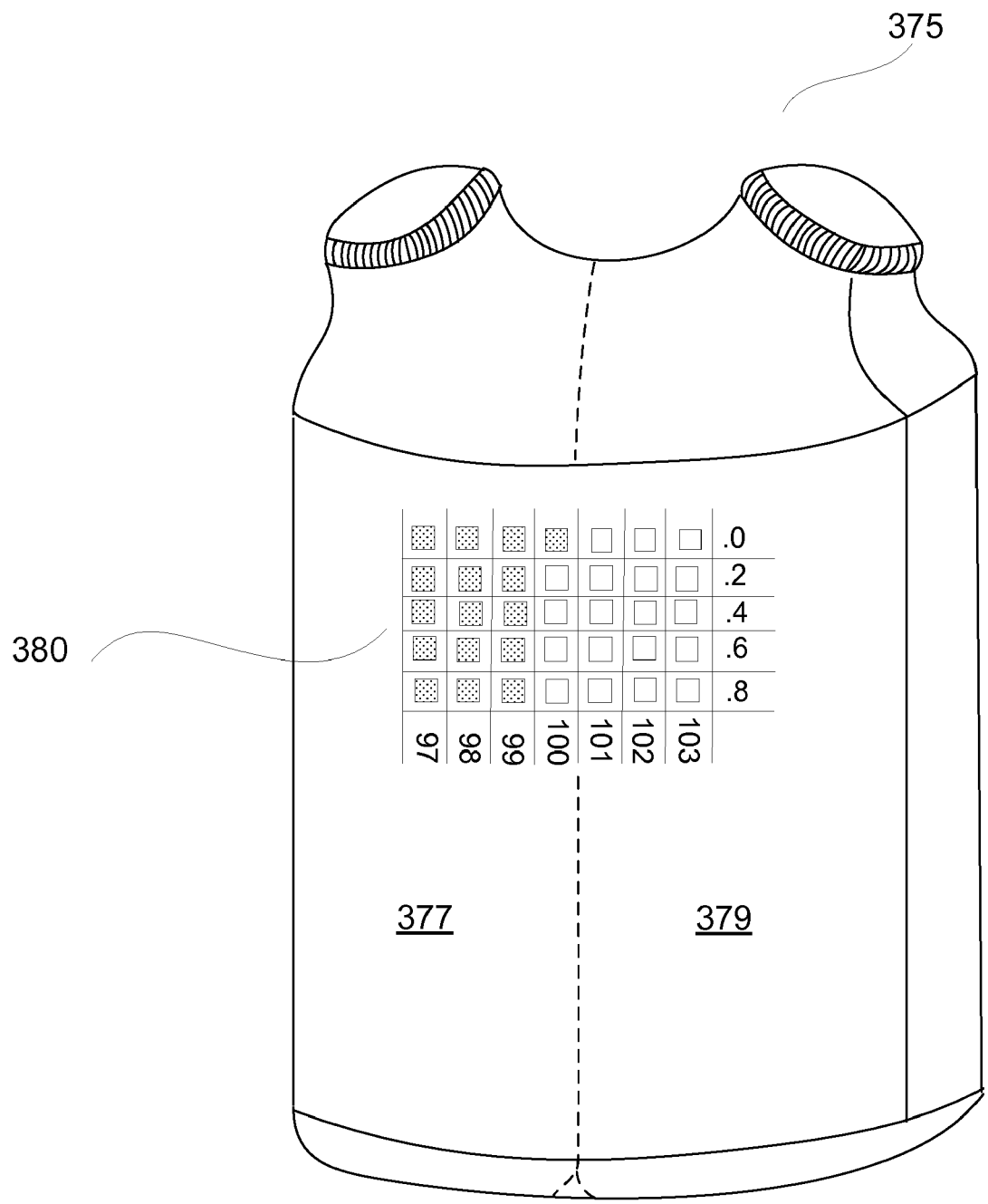
FIG. 4B shows a bottle with two compartments and a thermometer according to one embodiment of the invention.

There can be multiple areas to store multiple substances. For example, FIG. 4B shows a bottle 375 with two compartments, 377 and 379, and a thermometer 380. The thermometer 380 can be implemented by a thermochromic paint, which can be insulated from the bottle 375 by a piece of thermally insulating material between the bottle 375 and the paint 380. This will prevent the paint from measuring the temperature of the bottle or materials in the bottle, instead of the person the paint is touching. The temperature sensor 380 includes a series of dots, arranged in an array with two axes. One axis is in one degree interval, and the other is in 0.2 degree interval. In the figure, the temperature is 99.2 degrees Fahrenheit. The temperature sensor 380 can be laminated into a label on the bottle 375. To use the thermometer 380, for example, the user can hold the bottle 375 against her forehead for a duration of time. Then the user pulls the bottle 375 away from the forehead to read the temperature. The bottle 375 shown includes two compartments. One compartment 377 can be for medication, and another compartment 379 can contain a type of beverages, such as water, for the user to drink.

In one embodiment, the substance in a bottle is stored in a bag. When the substance is getting low and needs to be replenished, the user can order another bag of the substance and replace the old bag with the new bag, while using the same bottle.

In one embodiment, one or more compartments are detachable. For example, the compartment holding electrical components is detachable. The user can detach the electronic compartment and wash the bottle, such as with a dishwasher.

Figure 5A:
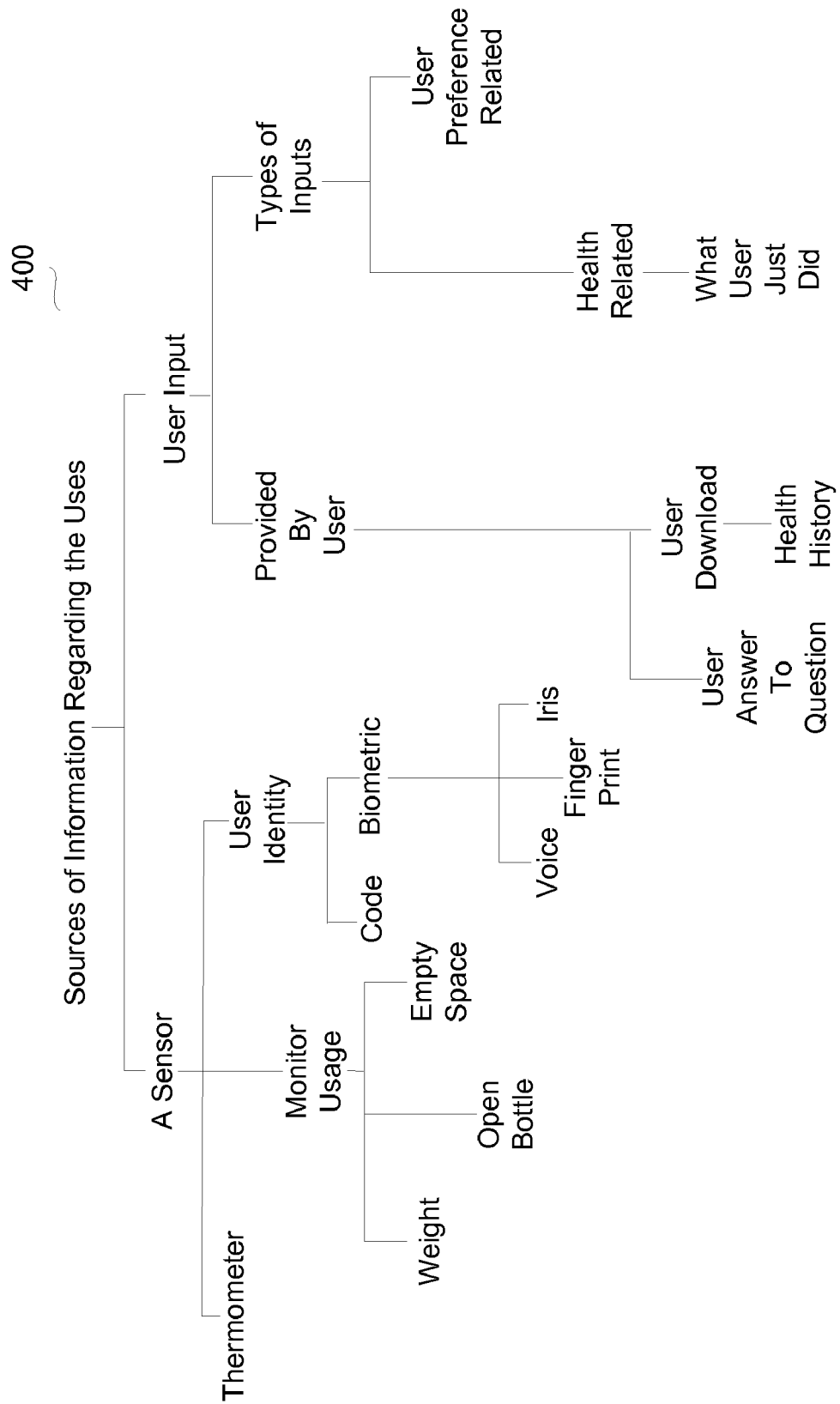
FIGS. 5A-5B show examples of the sources of the personal information in a bottle according to different embodiments of the invention.
Figure 5B:
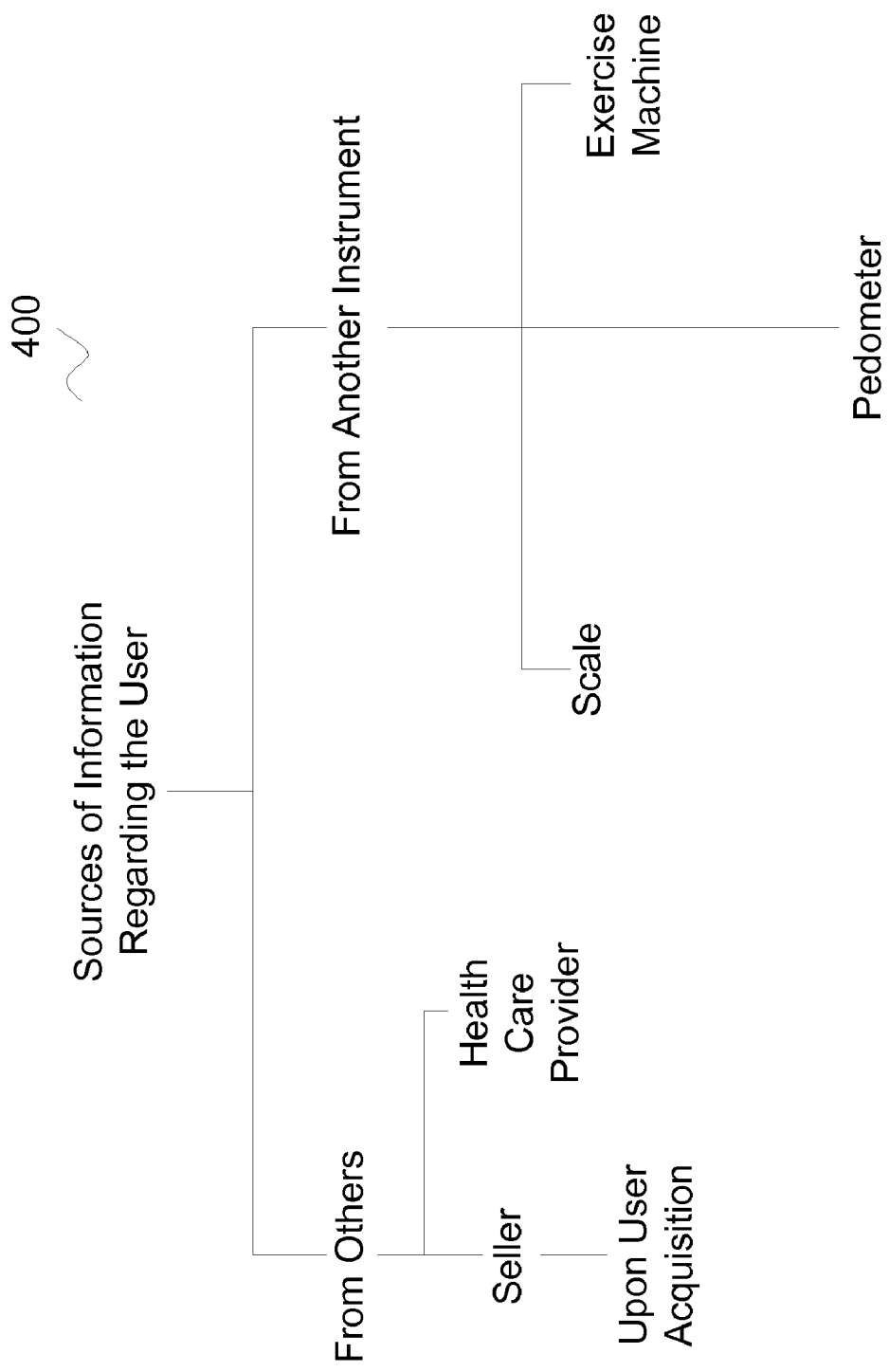

A bottle can hold information electronically regarding the user. The personal information of the user can come from different sources. FIGS. 5A-5B show examples of the sources of the personal information 400 according to different embodiments. In one embodiment, the bottle can be considered personal to the user if the bottle holds personal information of the user, such as electrically holds the information.

In one embodiment, the personal information is from a sensor. The sensor can be a sensor that measures a health condition of the user. As an example, the sensor is a thermometer. After temperatures are measured, the bottle keeps track of the measured temperature, which can include the time when each temperature was measured.

The amount of the substance that has been consumed by the user can be kept track of. For example, a scale can keep track of the weight of the bottle. As the user takes the substance, the weight of the bottle is reduced. The scale can be in a base that the bottle sits on. More discussion regarding the base will be found below. In this example, the bottle is assumed to be personal to the user, and only the user takes the substance in the bottle.

Another type of information regarding the user is the user's identity. In one embodiment, the bottle includes a biometric sensor that can be used to sense the identity of the user. The biometric sensor can be based on the user's voice, the user's fingerprint and/or the user's iris.

In one embodiment, a bottle includes a fingerprint sensor to serve as a key to access the information stored in the bottle. The fingerprint sensor can also serve as an on/off switch. As the user presses onto the sensor, the sensor is activated. If the sensor authenticates the fingerprint to be the fingerprint of the user, other electrical components in the bottle will be activated. Otherwise, the user cannot use at least one electrical component in the bottle.

In another embodiment, the bottle stores a code entered by the user, and the code can be used to identify the user. The code can be an alphanumeric string of characters. Upon entering the code, the user can use other electrical components in the bottle.

In one embodiment, the source of information regarding the user is from the user's input. For example, the user provides the inputs by responding to questions from a bottle. The bottle can present one or more questions to the user. Based on the user's responses to the questions, the bottle gathers information regarding the user. This can be done through a speaker and a microphone on a bottle, or through questions shown on a display of the bottle.

Instead of responding to questions from a bottle, in another embodiment, the user downloads information into a bottle. This can be done from, for example, a memory card or a computer. For example, the user can download information regarding his health history into a memory in the bottle.

There can be different types of inputs by the user. The inputs can be related to the condition of the user. For example, it can be the user's response regarding whether the user has eaten yet to find out if the user has an empty stomach before taking the content in the bottle. In one embodiment, the inputs can be related to the user's preference. For example, the inputs can be a piece of contact information, such as the cell phone number, of the user, or an email address of a healthcare provider. This allows the bottle to contact the person the user prefers, if the bottle has such capabilities. In another example, user preference includes the songs, or the tunes, which the user likes and/or dislikes. The songs can be downloaded into the bottle.

Information regarding the user 400 can be from another person or entity. In one embodiment, the information is from the seller or dispenser of the bottle with the substance inside. For example, when the user gets the bottle with medication from a pharmacy, a pharmacist can download information regarding the user into the bottle. There can be a barcode or other identifier that includes or points to information regarding the user, such as the user's name. The pharmacist can scan the barcode or use the other identifier. After capturing the information, the information can be downloaded to the bottle. As another example, the information is from a healthcare provider of the user. The user can go to see the provider, who can download information regarding the user into the bottle.

Figure 6:
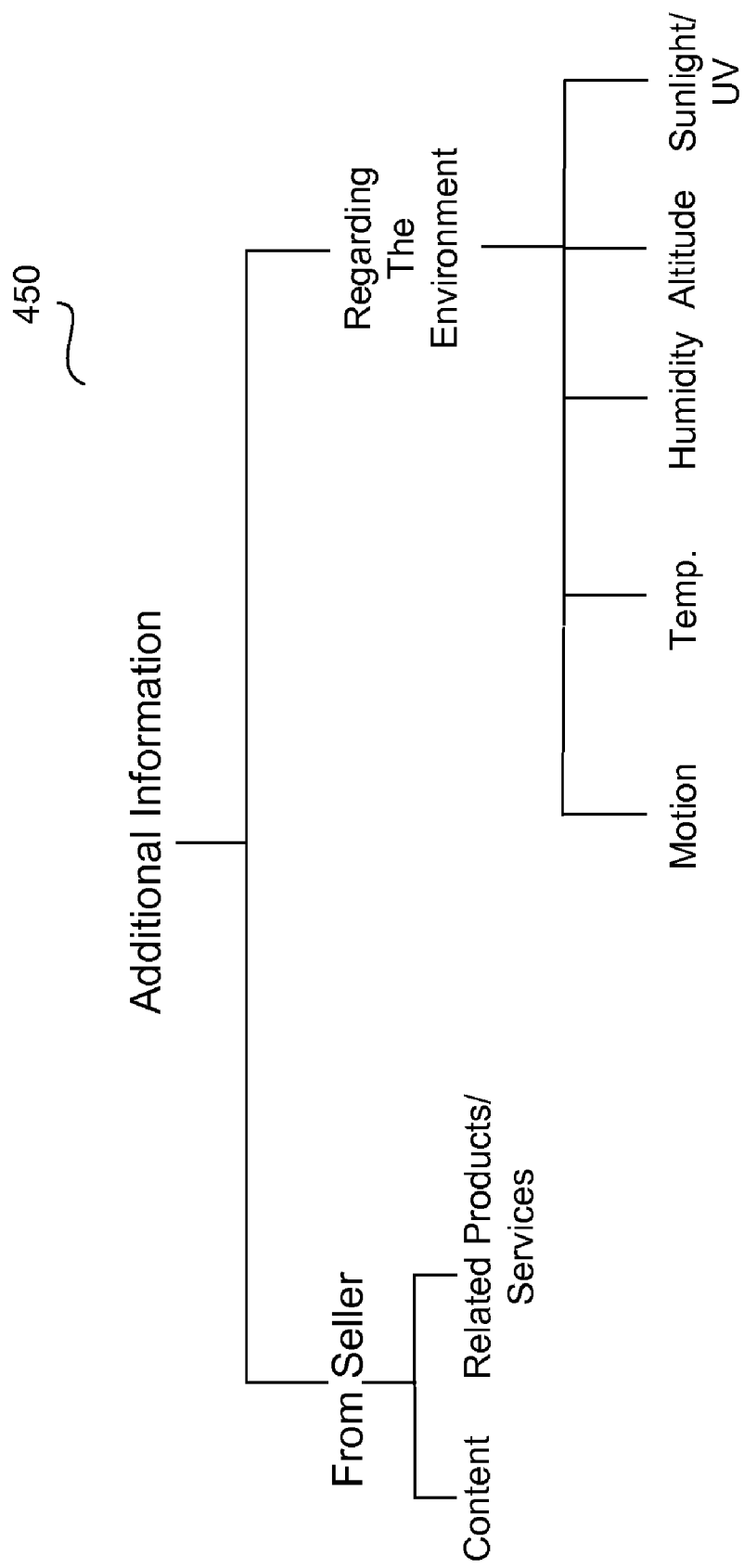
FIG. 6 shows examples of other types of information in a bottle according to different embodiments of the invention.

Instead of information regarding the user, the bottle can store other types of information. FIG. 6 shows examples of other types of information 450 in a bottle according to different embodiments. For example, the bottle can store information from a supplier of the bottle with the substance insider the bottle, such as a seller or a dispenser, regarding the content or the substance. The seller can be a drug company, and the dispenser can be a pharmacy or a drug store. These can be specific information regarding the substance, such as its side effects, precautions regarding the substance, its interactions with other drugs, health news related to the medication, and/or consumer awareness information. The information can be on products/services related to the substance provided, or other products/services provided, by the seller or the dispenser.

In one embodiment, a bottle also stores information related to the bottle's immediate environment. For example, the bottle keeps track of the information from a motion sensor in the bottle. The motion sensor keeps track of motions in the immediate vicinity of the bottle.

Figure 7:
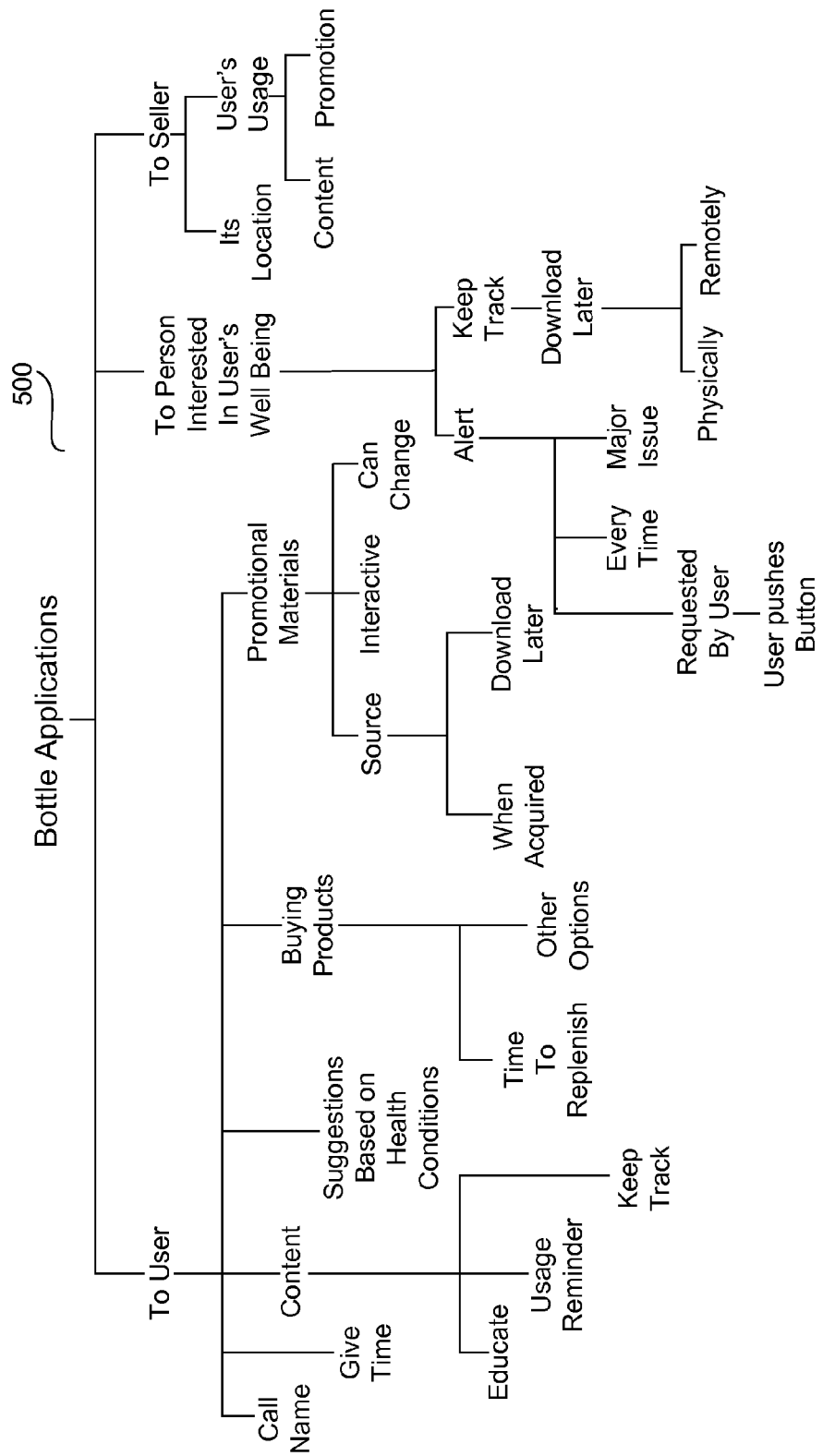
FIG. 7 shows examples of different applications by a bottle according to different embodiments of the invention.

FIG. 7 shows examples of different applications 500 by a bottle according to different embodiments. In one embodiment, the bottle provides information and/or recommendations to a user. For example, the bottle can announce the name of the user when the user activates the bottle. The bottle can give the user the time. The bottle can educate the user regarding the substance in the bottle.

In one embodiment, the bottle keeps track of the usage of the substance in the bottle. Based on the usage, the bottle can determine user compliance, or whether the user has been following the recommendation of a health care provider on when and how much to take the substance in the bottle. In another embodiment, the bottle can determine user abuse in taking the substance in the bottle. For example, the bottle carries a controlled substance, and the user can take significantly more than the recommended amount, in turn causing substance abuse. In yet another embodiment, the bottle can determine user mistakes, such as incorrect dosage being taken by the user.

In one embodiment, the bottle can remind the user when to take the substance in the bottle, how much the user should take, when the user should take again and/or reprimand the user for not taking the substance for a duration of time.

Figure 8A:
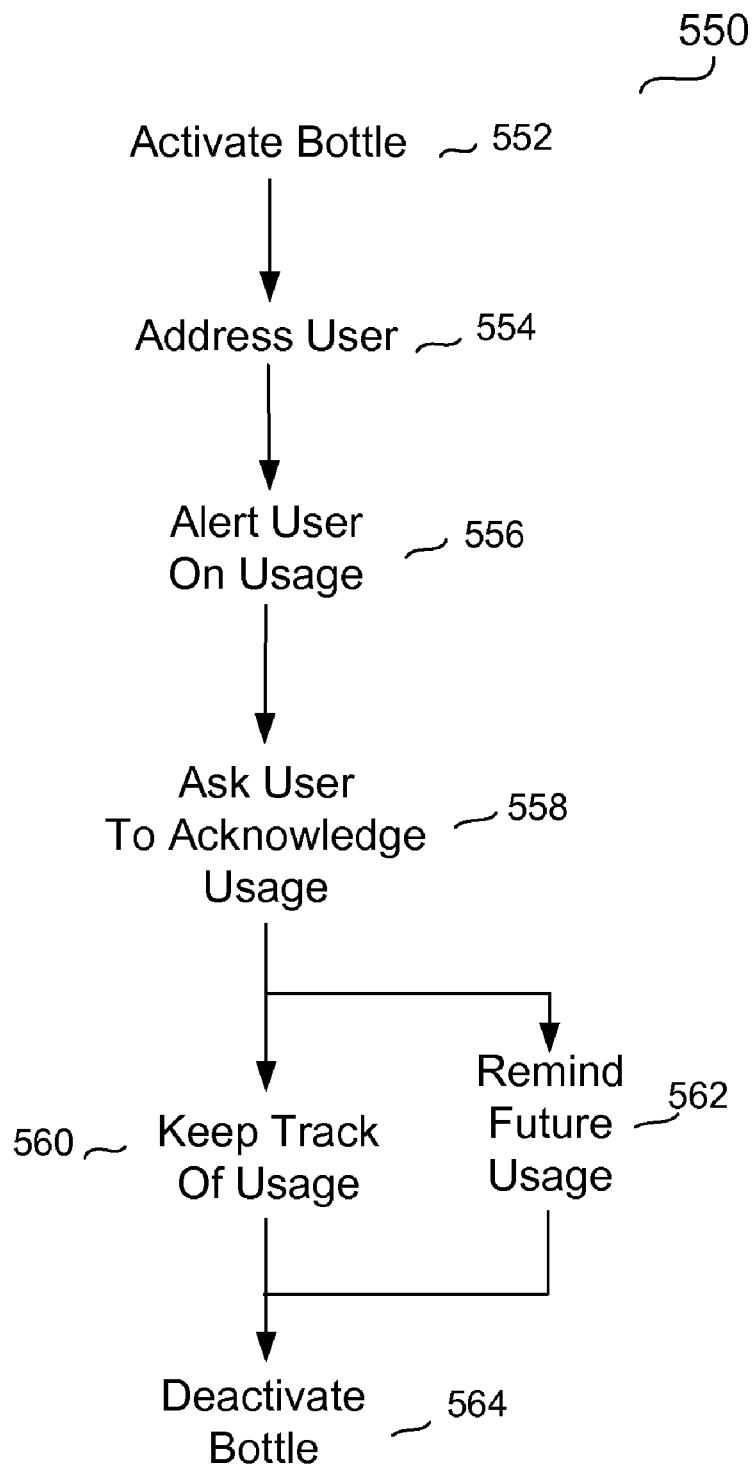
FIGS. 8A-8B show processes performed by a bottle regarding the use of the substance in the bottle according to different embodiments of the invention.

FIG. 8A shows a process 550 executed by a bottle regarding the use of the substance in a bottle according to an embodiment. The user activates 552 the bottle. This can be, for example, done by the user turning on the electronics in the bottle. Upon activation, the bottle addresses 554 the user. For example, the bottle says, "Hello, Angeline." Then, based on usage information, the bottle alerts 556 the user on usage, such as the user should have taken the medication in the bottle two hours ago. For example, the bottle says, "Angeline, you should have taken two tablets of Aspirin two hours ago." In addition, the bottle can ask the user if the user has eaten anything in the last hour because based on information regarding the medication, one should not take the medication with an empty stomach. For example, the bottle can ask the user, "Angeline, have you eaten anything in the last hour?" If the user answers "no", the bottle can tell the user to eat something before taking the medication. There can be a "yes"/"no" button on the bottle to allow the user to respond to queries from the bottle.

The bottle can also remind the user to acknowledge 558 the use of the substance in the bottle. For example, the bottle can say, "Angeline, after you have taken the tablets, please push the blue button on the bottle." After the user has taken the medication, the user can push the blue button on the bottle. This would facilitate the bottle to keep track 560 of information related to the user's usage. The bottle can also remind 562 the user when the user should be taking the substance. For example, the bottle can say, "Angeline, you should be taking two tablets of Aspirin in 4 hours, or around 5 pm today." With no other activities after a predetermined duration of time, the bottle deactivates 564 itself, such as by having its electronics go into a sleep mode or turning itself off.

Figure 8B:
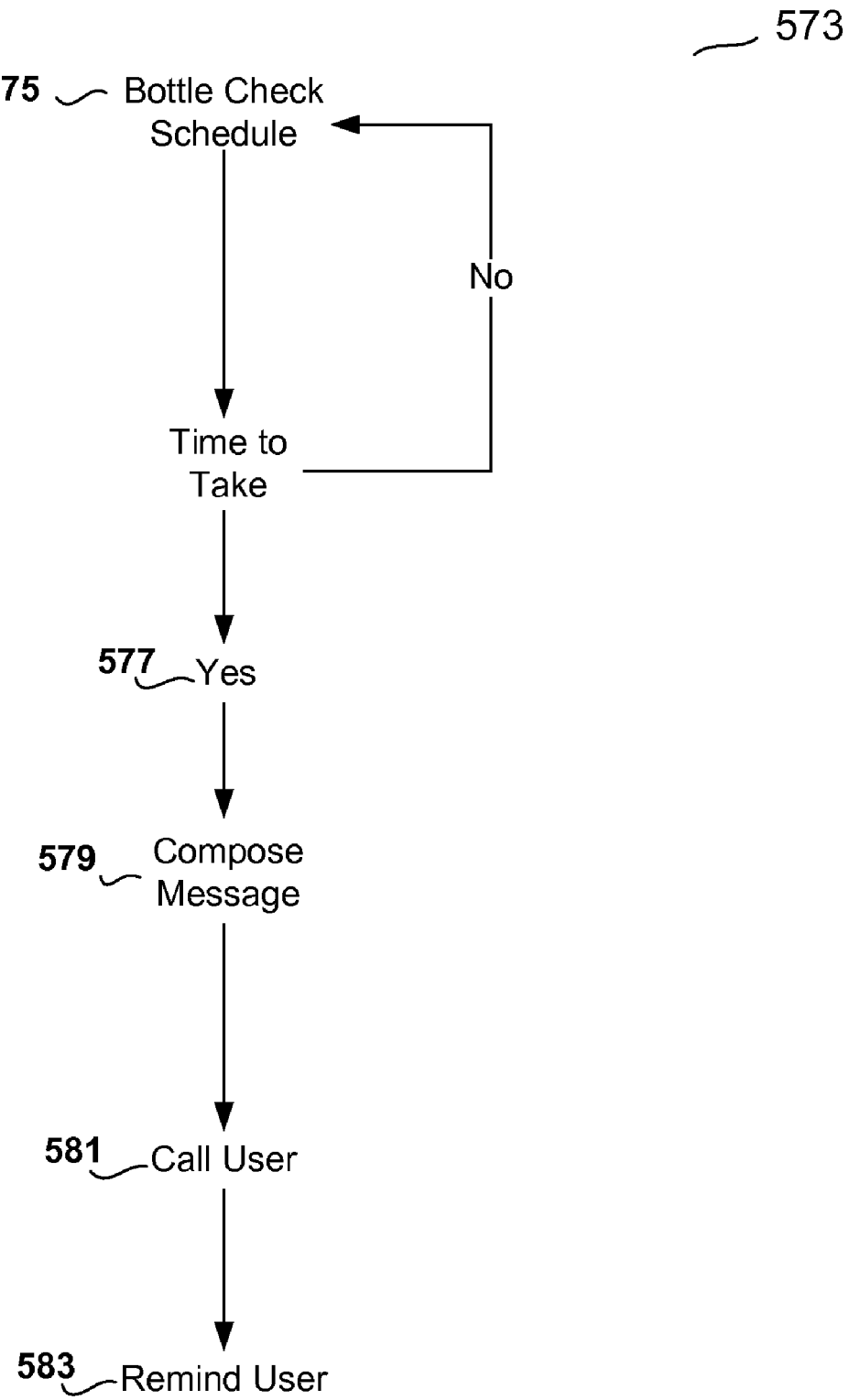

Instead of waiting for the user to activate, the bottle can proactively send a message to the user, or to another person or entity. FIG. 8B shows a proactive process 573 executed by a bottle according to one embodiment. In this example, the proactive process is related to sending a message. For example, the bottle checks 575 a medication schedule of the user to determine if it is time for the user to take medication. If it is not the time yet, the bottle waits. If it is time 577, the bottle will compose a message 579 for the user. For example, the bottle can include a number of templates. One template can be as follows: "[Name], this is your friendly [medication] bottle calling. Time to take your medication." Instead of just saying the medication, the prescribed amount can also be included in the message, such as two pills. The bottle can retrieve the appropriate template, and enter the user name, the medication name, and other relevant information into the template. The bottle can also retrieve a phone number. The phone number can, for example, be a cell phone number, or a desk/wall wired phone number. This phone number may be entered, for example, by the user or the user's healthcare provider. The bottle then composes 579 the message, which can be, "Tom, this is your friendly Aspirin bottle calling. Time to take two pills!" After the composition, the bottle calls 581 the user, and reminds 583 the user by sending the user the composed message.

In one embodiment, the user can be reminded by different types of songs or ring tones. If the user takes the medication at the right time, the bottle can reward the user with a happy song, or a song that the user likes. If the user takes the medication at the wrong time or takes the wrong amount, the bottle can reprimand the user with a sad song upon identifying the mistake. In another embodiment, the bottle can remind the user when it is time to take the medication with a pleasant song. If the user ignores the reminder and does not take the medication for a preset duration of time, the bottle can play an annoying song. The different types of songs, or sound clips, which can be a few seconds of a song, can serve the functions of rewards/punishment and/or motivation for the user to take the medication at the appropriate time.

In one embodiment, the bottle can allow the user to record messages, which can be voice messages. These messages can be time-stamped. These messages can also be linked to measurements made by the sensor, such as the thermometer. For example, after the user has measured his temperature, the user can record a message as to how he feels. Such information can be recorded for later retrieval.

The bottle can help the user regarding buying products. For example, the bottle can keep track of the amount of the substance in the bottle. When the content is getting low, the bottle can remind the user that it is about time to replenish. The bottle can provide suggestions to the user as to alternative substances to acquire. This suggestion can be based on the user's characteristics. For example, the user typically has high fevers. Based on such information, the bottle can suggest the user to buy Motrin, instead of Aspirin. In one embodiment, the bottle can upload such information to another device, such as a computer, which can add Motrin to other medications the user needs, to assemble a list. Next time when the user is about to go to a drugstore, the user can access the updated list from the computer as a reminder.

In one embodiment, the bottle can provide promotional materials to the user. The materials can be an advertisement shown on a display on a bottle to promote products and/or services offered by a company. Such products and/or services can be related to the substance in the bottle. The promotional materials can be from a supplier of the bottle with its substance. They can come with the bottle when the user buys the bottle. Or, they can be downloaded to the bottle after acquisition. For example, the user can connect the bottle to the company's website to download such information into the bottle. In one embodiment, when the user visits the website of the company, the user may be encouraged to connect the bottle to the website, such as through a connector on the bottle. The company can give incentives to the user if the user is willing to allow the company download company information onto the bottle. The incentives, for example, can be discounts for the company's products, which can include services.

In one embodiment, the product promoted can change. This change can be based on time. For example, every week the display can change the product shown, such as the display showing a type of health tea on one week and automatically changing to a type of vitamin the next week. The type of product promoted, such as the vitamin, can be more suitable for the user as indicated by the measurements from a sensor coupled to the bottle, such as the thermometer.

In one embodiment, the promotional materials can be interactive. There can be embedded hyperlinks and/or pop-up windows in the promotional materials, which allow the user to interact with the promotional materials.

In one embodiment, a bottle can provide information and/or recommendation to a person or entity interested in the well being of the user, such as a relative, a healthcare provider, a doctor, a nurse, a social worker, or the police.

The bottle can keep track of the user, such as the user's temperature to assist, for example, a healthcare provider. Such information can be stored in the bottle for future download. The download can be done remotely or locally. For example, the user can download the information to the healthcare provider's website through the user's computer. Or, the user can take the bottle to see the healthcare provider, allowing the healthcare provider to access the stored information. In another embodiment, such information can be wirelessly sent, such as through a cellular connection, to the person interested in the well-being of the user. In yet another embodiment, the person can also access the information wirelessly such as, by cellular connection. This can be done, for example, by allocating a cellular phone number to a cellular phone embedded in a bottle, which can allow the person to directly access the information.

In one embodiment, the bottle can send stored information to a person or entity interested when there is a critical issue. For example, if the temperature measured is beyond 104 degrees, the bottle can automatically send a message to the family doctor of the user. In another embodiment, the bottle can send an instant message to a relative of the user every time the user takes the substance in the bottle, or every time the user takes a measurement.

In yet another embodiment, the bottle can send information to a person or entity as requested by the user. For example, there might be a special button on the bottle. The button activates a special-purpose phone, such as when pushed, a special number will be dialed. In one embodiment, the most recent data, such as data captured within the last twenty four hours will be sent to the recipient.

In one embodiment, the bottle provides information and/or recommendation to a supplier of the bottle with the substance inside the bottle. For example, the bottle keeps track of its own location from the manufacturer to its dispenser or retailer and to the customer, such as from the big pharmaceutical company where the medication is produced, through the distributors, to pharmacies or hospitals. In one embodiment, such tracking can help ensure the drug produced is the same as the one being given out to the consumers; or such tracking reduces the chance of the drug produced being tampered with before reaching the consumers. Such tracking can also help reduce the problem of losing medical supplies or reducing the chance of having insufficient supplies of certain medication at hand. Such location information can be automatically forwarded to the entity interested, such as a hospital, distributor, manufacturer or pharmacy.

In another embodiment, the supplier can be aware of the user's usage. For example, a seller is aware of the substance getting low, or the seller can keep track of the usage of the substance each time the user uses it. In another embodiment, the seller is aware of the user accessing promotional materials, such as tracking the use of the hyperlinks and/or pop-up windows. This allows advertisers to gather information about what the user shows interest in (e.g. clicks on), and determine effects on sale of products. Such information can be transmitted to the seller through the bottle's electrical connection, for example, through the bottle's wireless connections.

Figure 9:
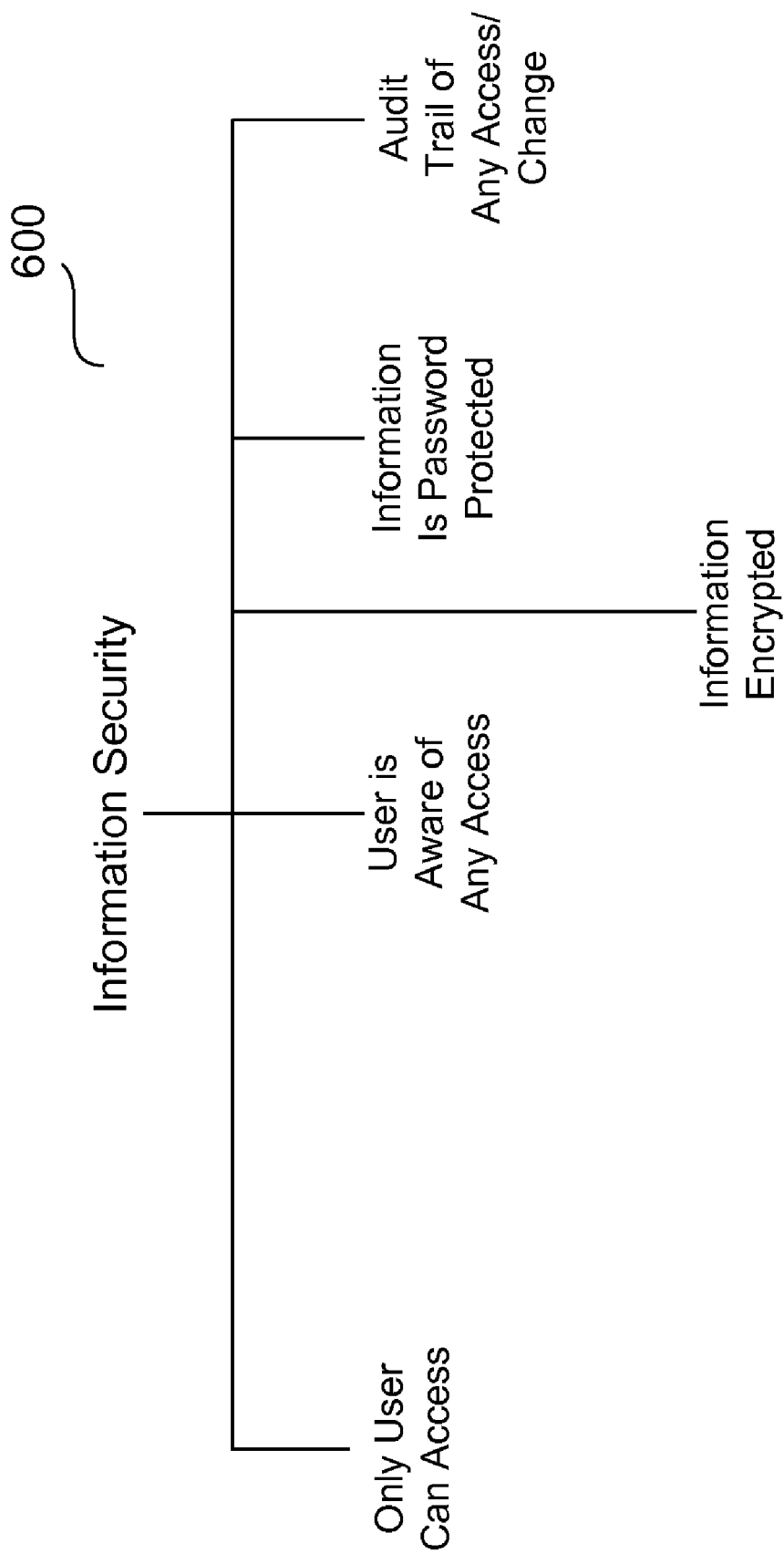
FIG. 9 shows examples of different attributes on information security regarding a bottle according to different embodiments of the invention.

Information stored in the bottle can be sensitive, particularly to the user. FIG. 9 shows examples of different attributes on information security 600 regarding a bottle according to different embodiments. In one embodiment, the information is secured. For example, only the user can access the information. This can be based on a biometric sensor. The information can be password protected. A code (e.g. password) can be entered to activate the bottle or to allow a person to access information in the bottle. In one embodiment, the information is encrypted. One needs the right key to decrypt the information in order to use it.

In another embodiment, the user is aware of any access. This can be whenever the information is accessed. For example, the bottle can send the user an electronic message whenever any of the information is being accessed. In another embodiment, the bottle keeps track of data access and changes made to the data. Such information can serve as an audit trail.

A number of embodiments have been described regarding functions performed by a bottle. In one embodiment, a bottle is defined as a container or a receptacle that has a narrow neck. In another embodiment, a bottle is defined as a container or a receptacle with a width that is not uniform (some part narrower than another part, such a neck portion being narrower).

In yet another embodiment, a bottle does not have to have a narrow neck and a bottle can have uniform width or substantially uniform width, but the bottle has an opening or a mouth that can be plugged, corked or capped. For example, the cap can be removed to expose the opening or the mouth. In still another embodiment, a bottle is portable if it can be carried or moved with ease by a person. In yet another embodiment, a bottle is portable if it can be handheld, meaning that it can be easily grasped and/or carried within a single hand.

Figure 10:
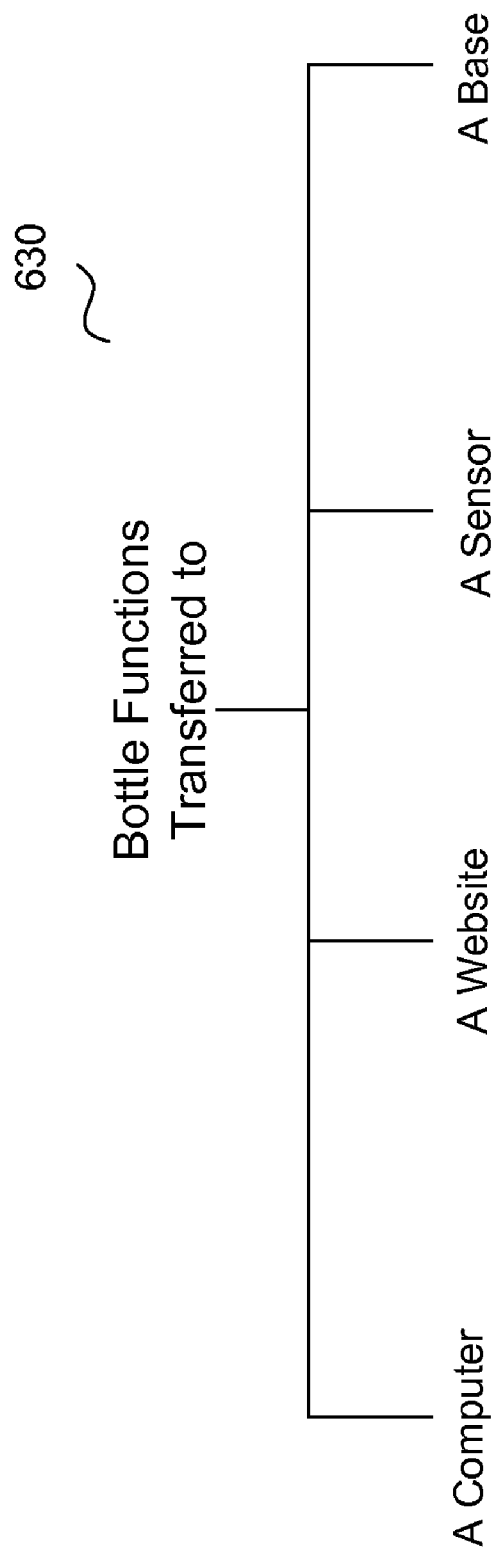
FIG. 10 shows examples of at least a portion of the functions previously described as performed by a bottle being performed by another device, according to different embodiments of the invention.

FIG. 10 shows examples of at least some of the functions previously described as performed by a bottle, being performed by 630 another device. In one embodiment, a number of the functions are performed by a computer coupled to a bottle, through, for example, a connector at the bottle. In another embodiment, instead of a computer, a number of functions are performed by a remote website, wired or wirelessly coupled to the bottle. In yet another embodiment, instead of the bottle, a number of functions are performed by a sensor, such as a thermometer, coupled to the bottle.

Figure 11:
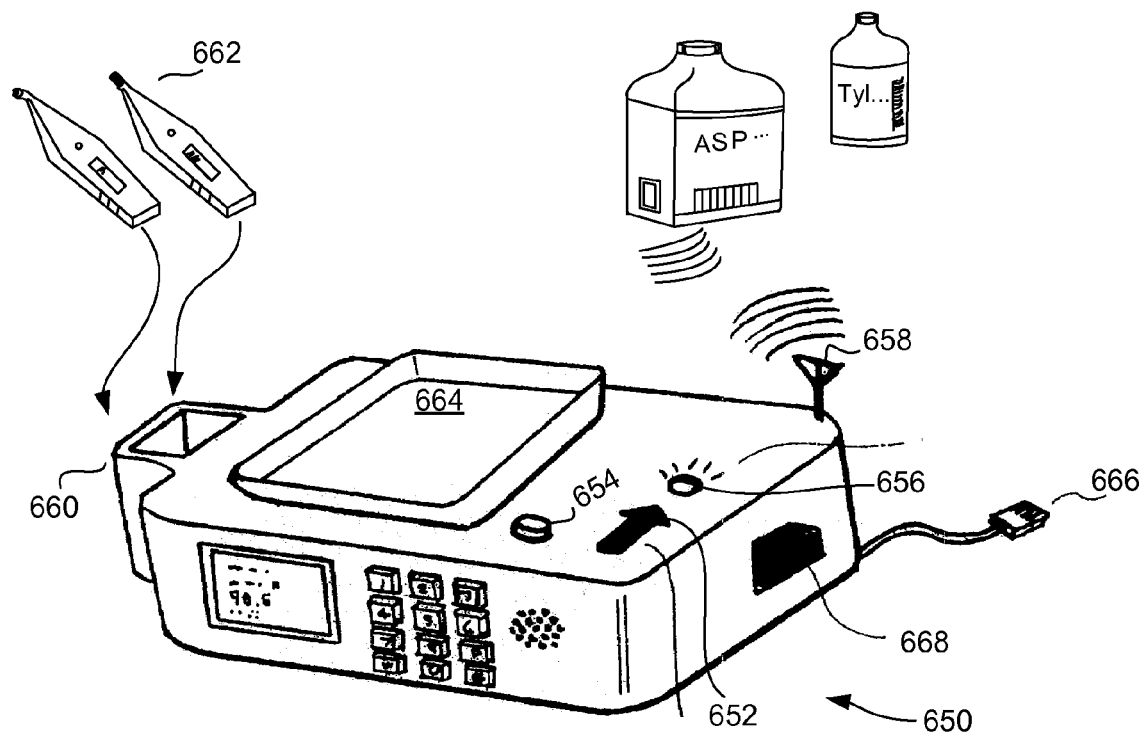
FIG. 11 shows an embodiment of a base for a bottle according to one embodiment of the invention.

In one embodiment, any of a number of functions previously described as being performed by a bottle can be performed by a base. FIG. 11 shows one embodiment of such a base 650, which can be electrically coupled to a bottle.

In one embodiment, in such a base implementation, operations performed by a bottle can be minimized. For example, when the user gets his medication from a pharmacist, the bottle can include information regarding the prescription, which can include the user's schedule to take the medication. Such information can be on a barcode, a RFID tag or in a memory in the bottle, according to different embodiments. The user can download such information into the base. For example, if the information is in a barcode on a bottle, the base can include a barcode reader 652. The user can push a start button 654, and then the user can scan the barcode to enter such information into the base 650. When the barcode is successfully scanned, a signal can be provided to the user, such as a light 656 can turn on, or a signal can be provided by a speaker.

Note that different pharmacies might use different barcodes. In one embodiment, information regarding different barcodes from the different pharmacies is stored in the base.

In one embodiment, the base can include a RFID tag reader, including its antenna 658, to access the information stored in an RFID tag.

Alternatively, the bottle can include an electrical connector. The user can connect the bottle's connector to a base connector to download the information. In one embodiment, the bottle's connector is at the bottom of the bottle. There can be a recessed space on top of the base to receive the bottle. When the user puts the bottle into the space, with the bottle's connector received by the base's connector, information in the bottle can be downloaded into the base. In one embodiment, the bottle's connector can be at the bottom of the bottle. The bottle's connector can be a standard connector, such as a USB connector. The connector can be slightly recessed into the bottle, allowing the bottle to firmly stand on a flat surface, without the connector sticking out.

In one embodiment, the base includes a slot 660 to receive a sensor 662, such as a thermometer. The slot 660 can be used to track different measurements regarding the user. Each time a sensor is stationed in the space, such as inserted into the slot 660, measurements made by the sensor 662, such as in the past 24 hours, are uploaded to the base 650. The upload can be through a connector at the sensor 662 with a corresponding connector at the base 650.

In one embodiment, the base 650 can also include a scale 664. The user can weigh a bottle with the scale 664. The scale 664 can also be at a recessed space on top of the base 650 to receive the bottle. In another embodiment, as the bottle sits on the scale 664, its RFID tag is read by a RFID tag reader in the base 650.

In another embodiment, the base can have multiple recessed spaces for more than one bottle. The base can also have multiple slots for more than one sensor to be stationed.

In another embodiment, the base 650 can include a connector 666 to connect to other devices or instruments, such as a computer. Instead of a physical connector, the connection can also be wireless. Based on such connections, the base 650 can be connected, for example, to another area, such as a website. Information in the base 650 can be accessed and the base 650 can also access information from the another area, such as the website. In yet another embodiment, the base can also include another input/output connector 668, which can be for a memory device, such as a flash memory card.

In one embodiment, the base can keep track of the time, the date, the weight of a bottle, the medication, sensor measurements and/or the user identity. For example, every time the user uses a bottle of medication, the user can place the bottle on a selected space on the base to weigh the bottle and to download information into the base. This would allow the base to keep track of information related to the user taking the medication.

In one embodiment, since the bottle can keep track of the type of substance taken by the user, as the user takes different types of substances, such as from different bottles, the information regarding the substance can be downloaded into the base accordingly. Based on information in the base, or information accessed from a remote site or area, the base can provide indication to the user that the different types of medication the user is taking, conflict with each other and can cause complications to the user.

In one embodiment, a base is, or performs the functions of, a medical monitoring system. In another embodiment, a base can be considered personal to the user in the sense that the user typically does not want to share it with another user if the another person is using the base for similar purposes as the user. This can be similar to a toothbrush, which is usually considered personal to the user. However, the user may be willing to let a healthcare provider use it because the provider is typically using the base for different purposes, such as to access information from it to diagnose the user.

FIG. 1 shows one type of thermometer to measure the user's temperature. FIGS. 12A-E show examples of other types of thermometers according to different embodiments.

Figure 12A:
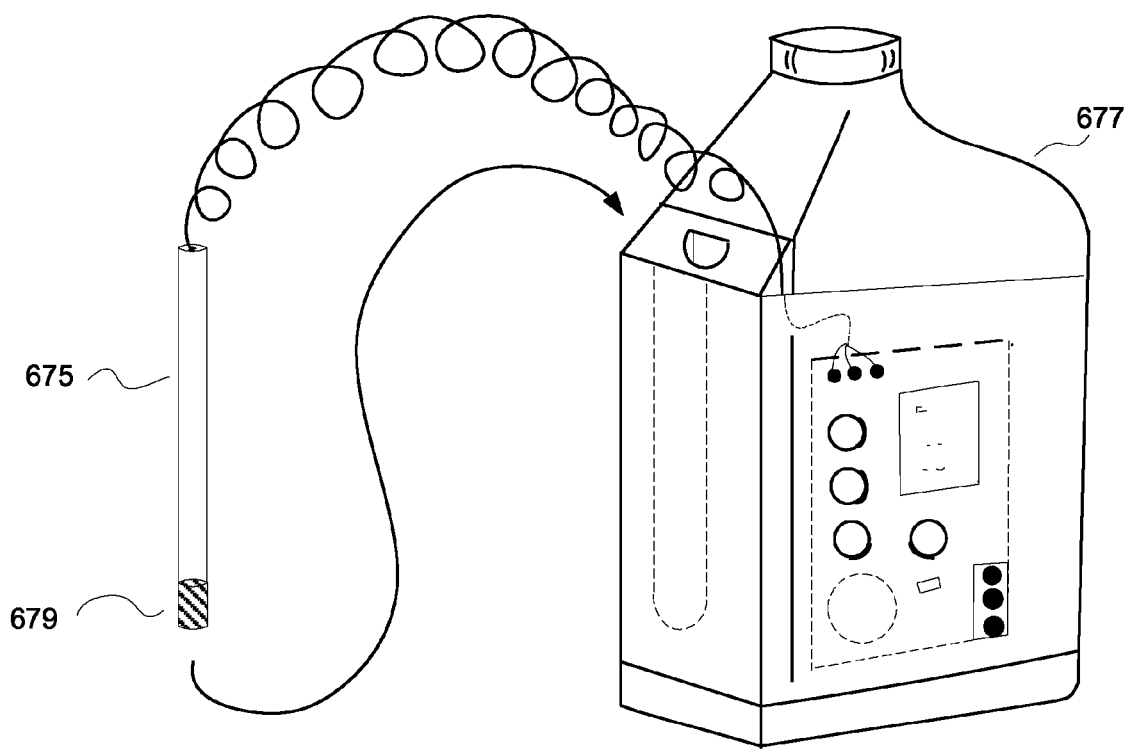
FIGS. 12A-12E show examples of other types of thermometers according to different embodiments of the invention.

In FIG. 12A, the temperature sensor 675 is tethered to a bottle 677. In this example, the temperature sensor 675 does not include any display. The temperature sensor 675 has a heat sensor 679 at its tip. The bottle 677 keeps track of temperatures measured.

Figure 12B:
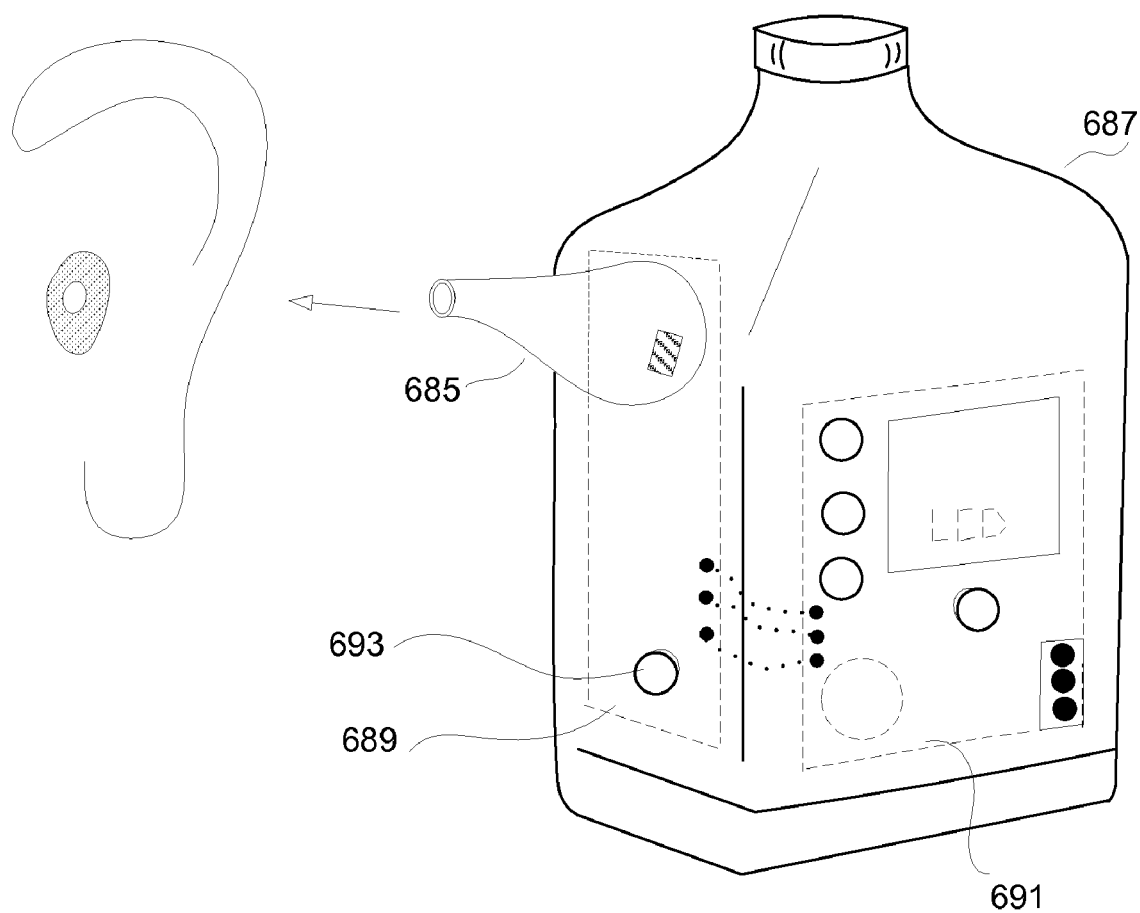

FIG. 12B shows an infrared ear thermometer 685 on a side surface of a bottle 687. In this example, the bottle 687 can include two printed circuit boards, 689 and 691, as shown. The on/off button 693 for the infrared ear thermometer 685 can be on the side surface circuit board 689. In another embodiment, the on/off button is located on the front surface circuit board 691.

Figure 12C:
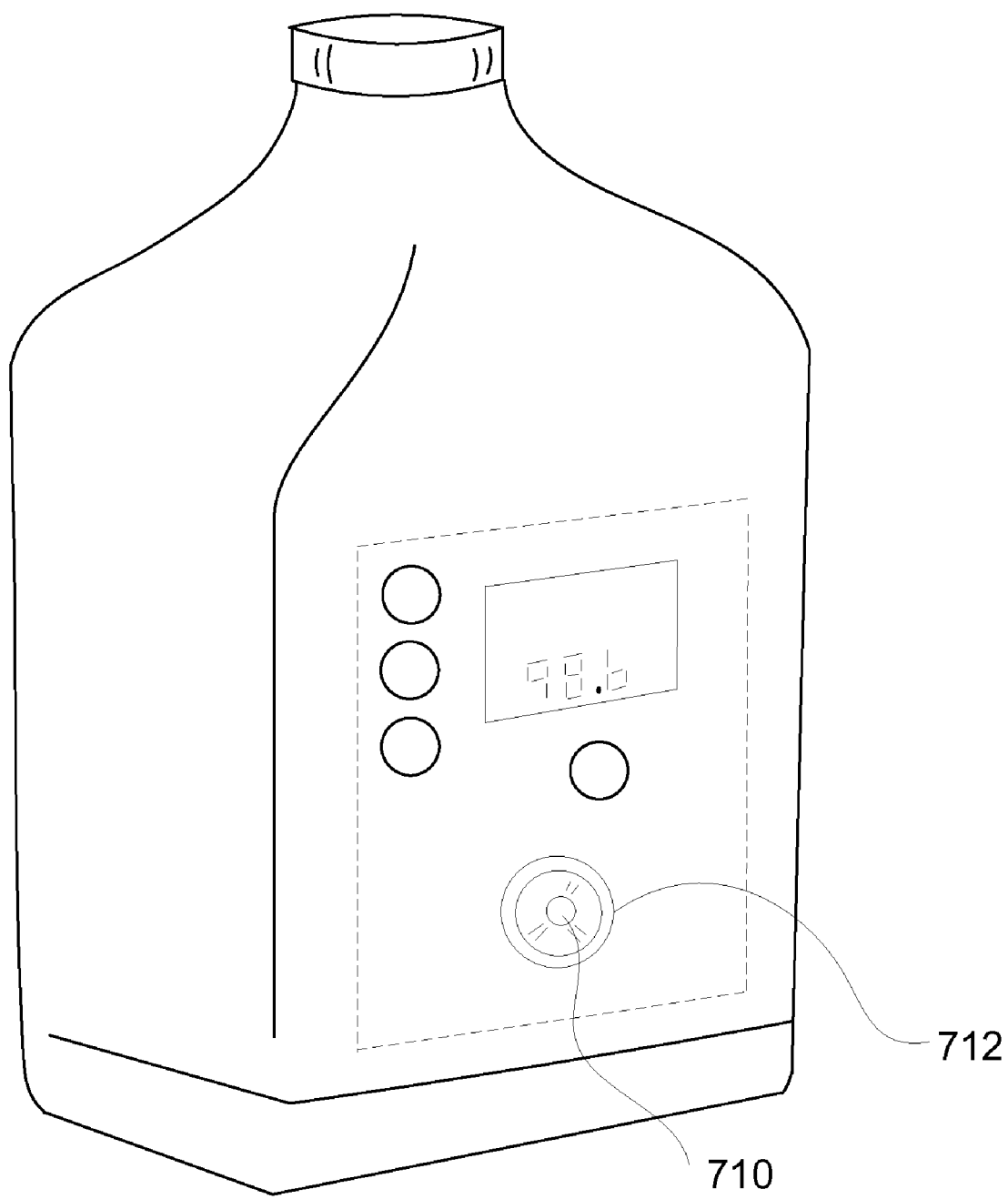

FIG. 12C shows an infrared sensor 710 in a ring structure 712 for measuring the temperature of a surface. For example, the surface can be the forehead of the user. Such sensors are known to those skilled in the art and are discussed, for example, in U.S. Pat. No. 6,292,685, which is hereby incorporated by reference in this application.

Figure 12D:
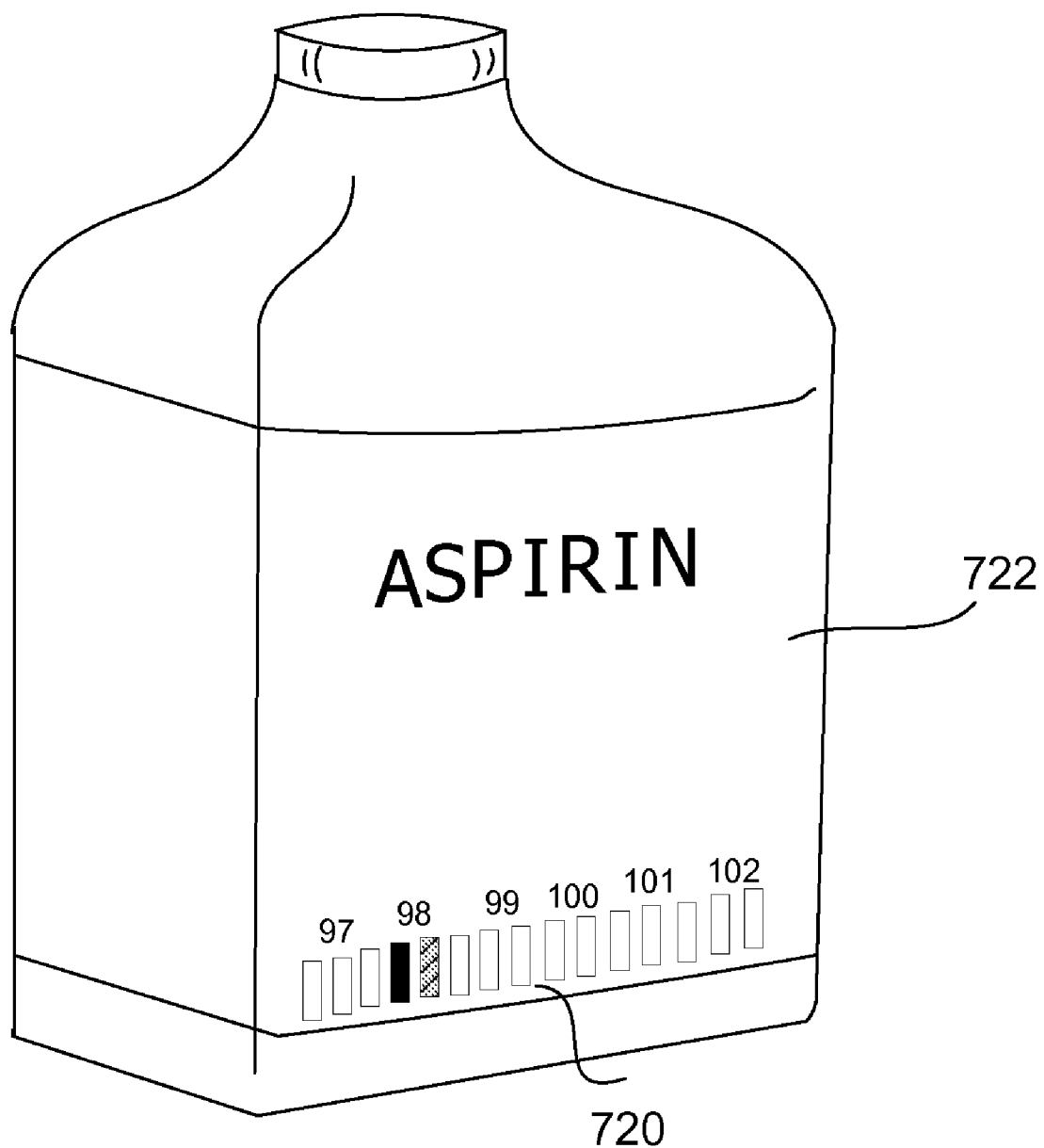

In FIG. 12D, the thermometer 720 is made of thermochromic paint attached to a surface of a bottle 722.

Figure 12E:
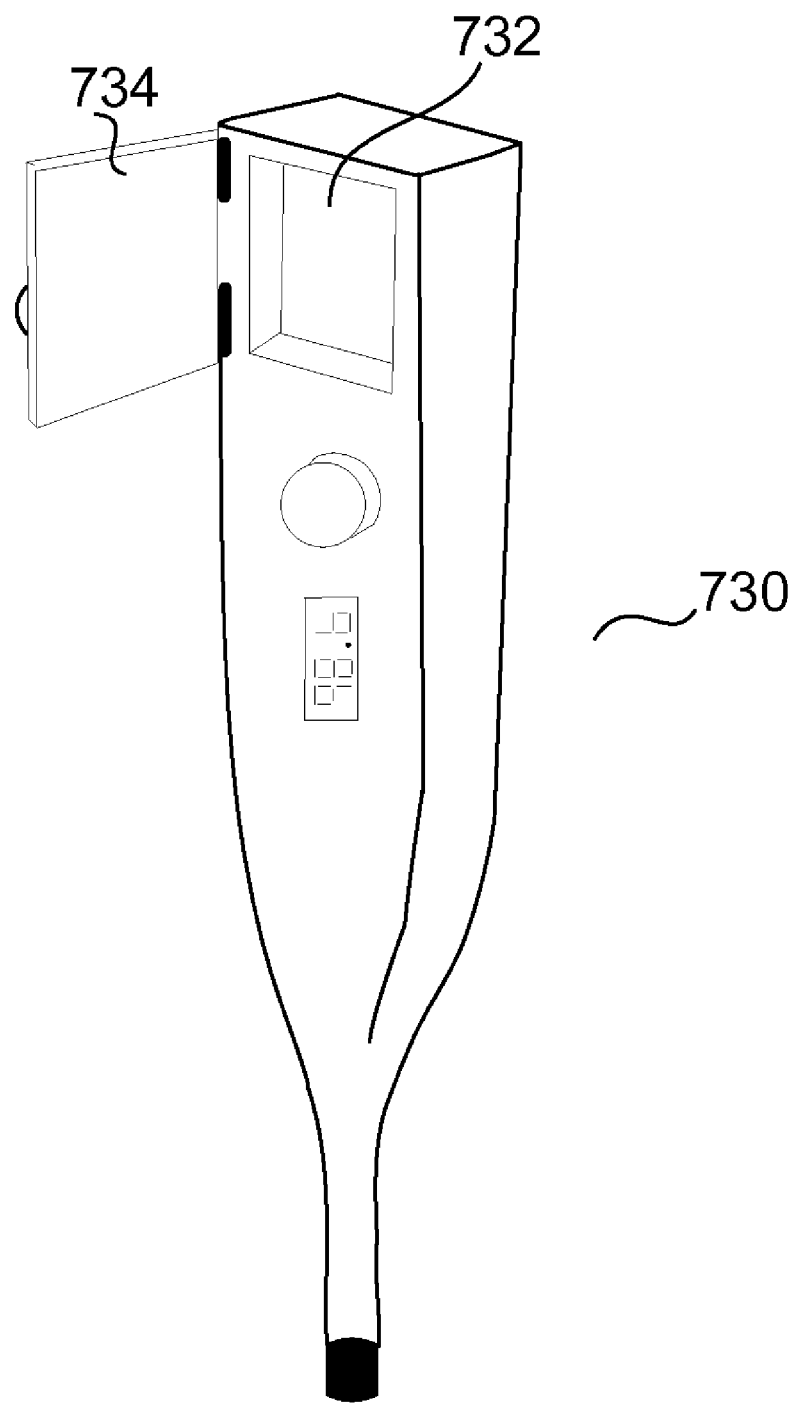

FIG. 12E shows a sensor 730 with a box 732 that has a lid 734. The box 732 can be used to carry pills or other medication, such as a pill box. The sensor 730 can also include an electrical connection, such as a physical connector or a wireless connection, to electrically couple the sensor 730 to another device.

Figure 13:
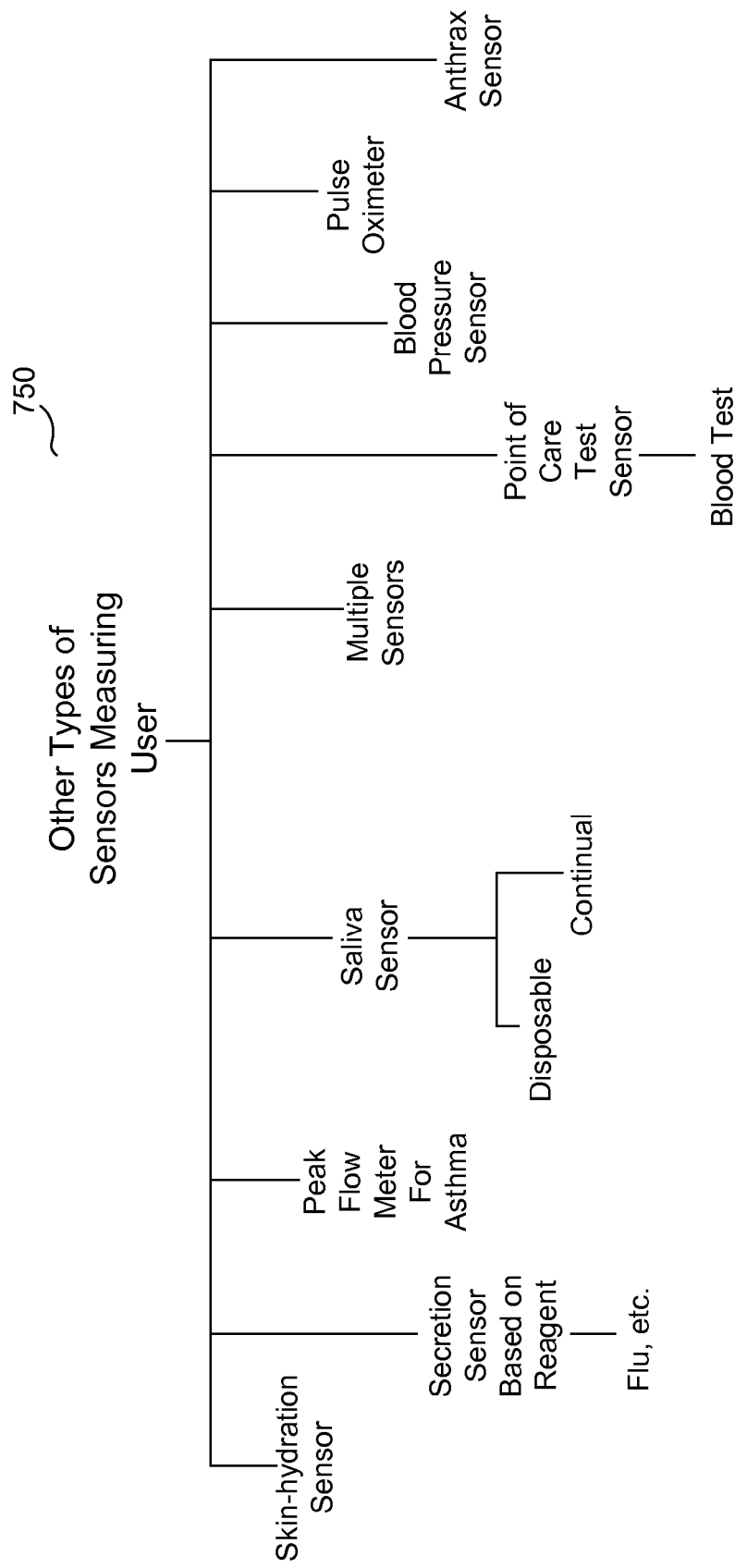
FIG. 13 shows examples of other types of sensors to provide different types of health information regarding the user according to different embodiments.

Instead of a thermometer, FIG. 13 shows examples of other types of sensors 750 to provide different types of health information regarding the user according to different embodiments. One or more of such sensors can be used with or without a bottle for the user. Different examples of such implementations have been described in U.S. Provisional Patent Application Ser. No. 60/670,957, entitled, "Bottle of lotion with a lotion sensor," which is hereby incorporated by reference.

In one embodiment, the sensor is a skin hydration sensor or a lotion sensor and the bottle is for holding lotion.

In one embodiment, the sensor is a blood pressure monitor. In another embodiment, the sensor is a pulse oximeter.

In yet another embodiment, the sensor is an anthrax sensor, such as using PCR based test, which can be applicable to a bio-terrorism environment. The corresponding bottle can carry the antibiotics against anthrax.

Figure 14A:
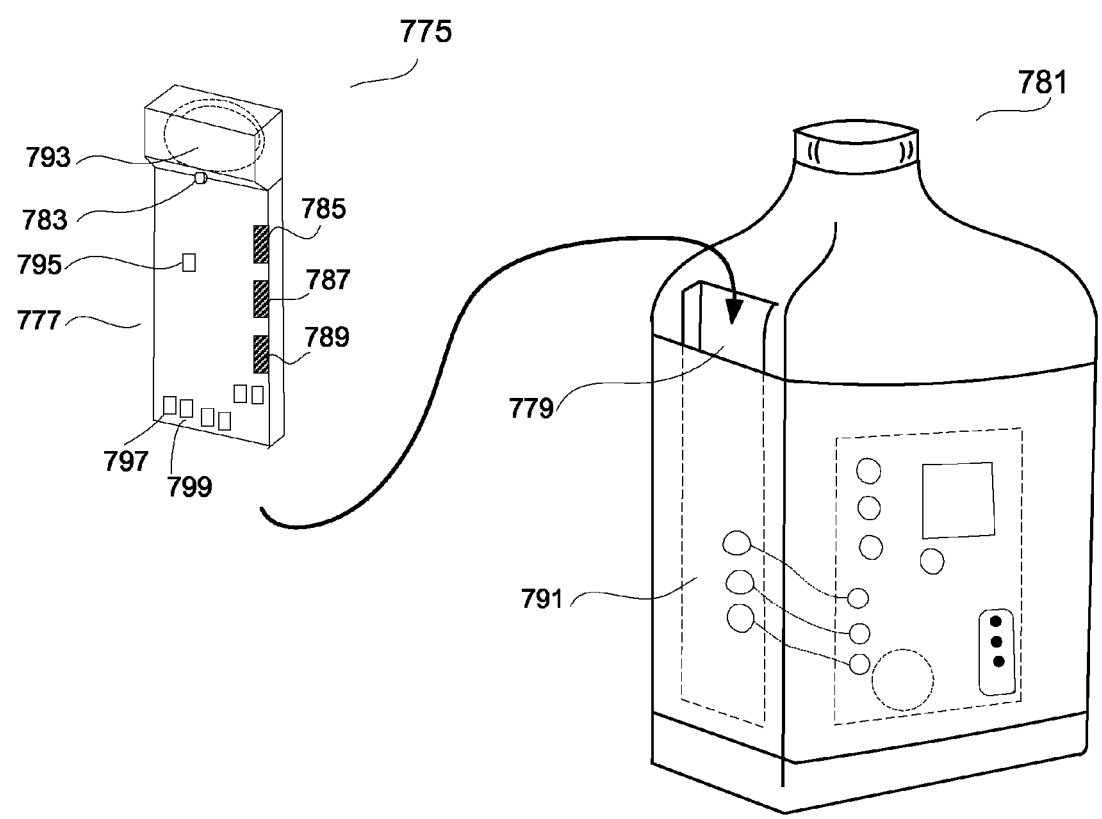
FIGS. 14A-14C show examples of reagent sensors sensing a secretion according to different embodiments of the invention.
Figure 14B:
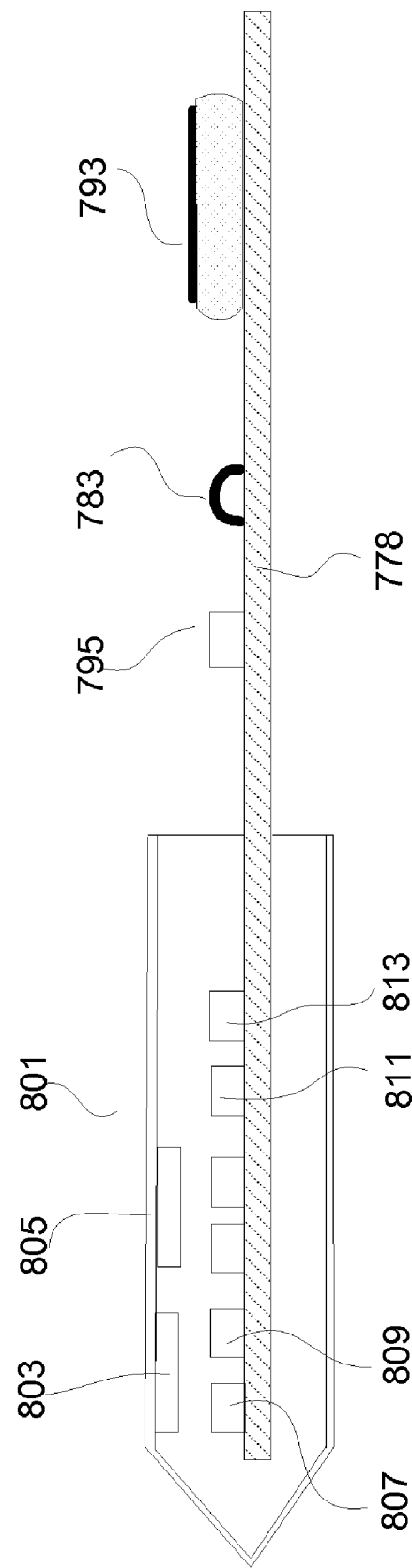
Figure 14C:
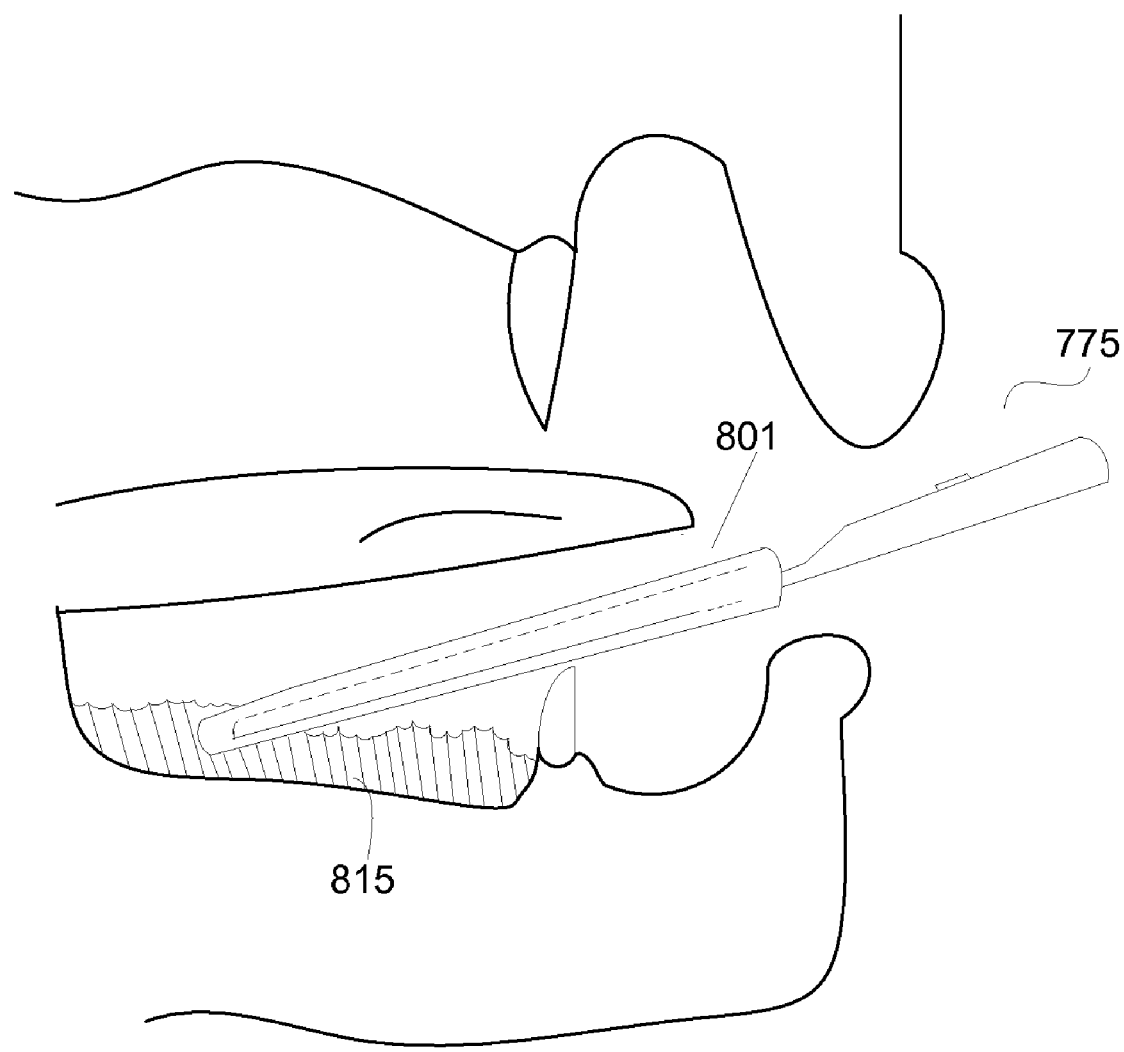

In one embodiment, the sensor is a secretion/excretion sensor based on a reagent, and the bottle holds medication, such as, for example, for flu/cold/strep-throat. The secretion/excretion can be, for example, saliva, sweat, urine, or stool, depending on the embodiment. FIGS. 14A-C show different embodiments of a reagent sensor according to different embodiments, with the sensor 775 including a sensor head 777 and a disposable sensor tube 801 carrying reagents.

As shown in FIGS. 14A-B, the sensor 775 includes a sensor head 777 adaptable to be inserted into a slot 779 of a bottle 781. The electrical components of the sensor head 777 can be on a printed circuit board 778. The board includes an on/off switch 783 to activate the head. The board also includes a number of connecting pads 785, 787 and 789, to electrically connect to a number of corresponding pads 791 at the bottle 781. The board can also hold a battery 793 as a power source, and a microcontroller unit 795 to control operations.

In one embodiment, the sensor head 777 includes a number of light emitting diode and photodiode pairs, such as 797 and 799. For example, there can be two such pairs, each pair for one type of reagents. To be explained below, an extra pair of light emitting diode and photodiode pair can be used to identify the reagents. In another embodiment, the extra pair can serve as a base line of the electrical measurements.

In one embodiment, the sensor tube 801 includes reagents 803 positioned or printed on a piece of absorptive material, such as a filter paper 805 that is in the form of a tube or envelope. The reagents are on the inside of the tube 801. There can be a piece of plastic or other transparent materials covering the reagents. The transparent materials can serve as the inner lining of the tube and can serve to provide structural strengths for the tube. The tube creates a channel to receive at least a portion of the sensor head 777.

An alignment mechanism can indicate that the tube 801 and the sensor head 777 are at the appropriate locations relative to each other. In one embodiment, the alignment mechanism is based on pushing the sensor head 777 all the way into the end of the channel of the tube 801. At that position, each LED and photodiode pair is approximately aligned to their corresponding reagents, such as the pair 807 and 809, with their reagents 803. When the LED emits light, the photodiode receives the light of the LED reflected from the corresponding reagents.

There can be markings on the filter paper. The marking, such as bar codes, can be used to indicate the identity of the one or more reagents on the filter paper. The extra LED 811 and photodiode 813 can be used to read the markings. For example, the markings can be printed barcodes that are read as the tube 801 is slid on or off the sensor head 777. In one embodiment, as the sensor head 777 is inserted into the channel of the tube, the photodiode 813 keeps taking measurements.

FIG. 14C shows one embodiment of the reagent sensor 775 in operation. The sensor head 777 is inserted into a sensor tube 801. The sensor 775 is then placed inside the mouth of the user. The saliva 815 goes through the filter paper and reacts with the reagents positioned on the filter paper. Depending on the chemicals in the saliva, specific reagents will change color. Such color changes can be captured by the one or more photodiodes, with the information stored in the reagent sensor 775. After the measurements, the sensor tube 801 can be disposed. In one embodiment, since a piece of plastic separates the reagents from the sensor head 777, the saliva does not wet the sensor head 777, and the sensor head 777 may not need to be washed after every use.

With the sensor tube 801 disposed, the sensor head 777 can be inserted back into the slot 779 at the bottle 781. Measurements made by the sensor head 777 can then be uploaded into the bottle 781.

In one embodiment, the secretion/excretion sensor based on a reagent can be used to measure the blood or other fluids of the user, based on different types of reagent.

In yet another embodiment, the sensor is a saliva sensor that can be used to determine whether a user is well hydrated. The corresponding bottle can hold a type of beverage. A number of embodiments regarding saliva sensing have previously been described in U.S. Provisional Patent Application, Ser. No. 60/670,957, entitled, "Bottle of lotion with a lotion sensor". The sensor can be disposable and the bottle can contain different types of beverages or fluids, which could include nutrients, vitamins, minerals, and/or medications. For example, the beverage can be vitamin C enriched water.

Figure 15A:
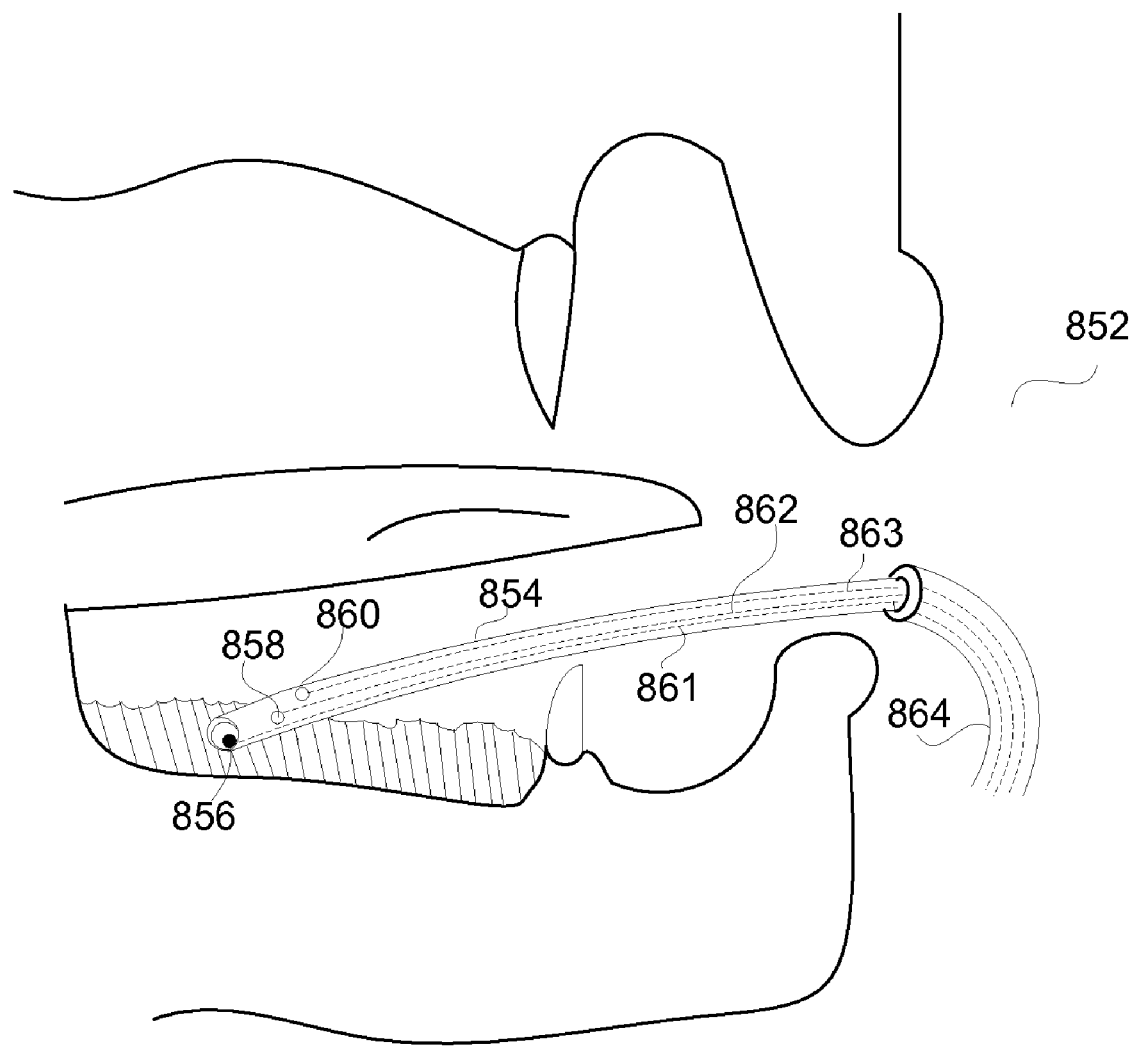
FIGS. 15A-15C show a saliva sensor that can continually sense certain attributes in saliva according to different embodiments of the invention.
Figure 15B:
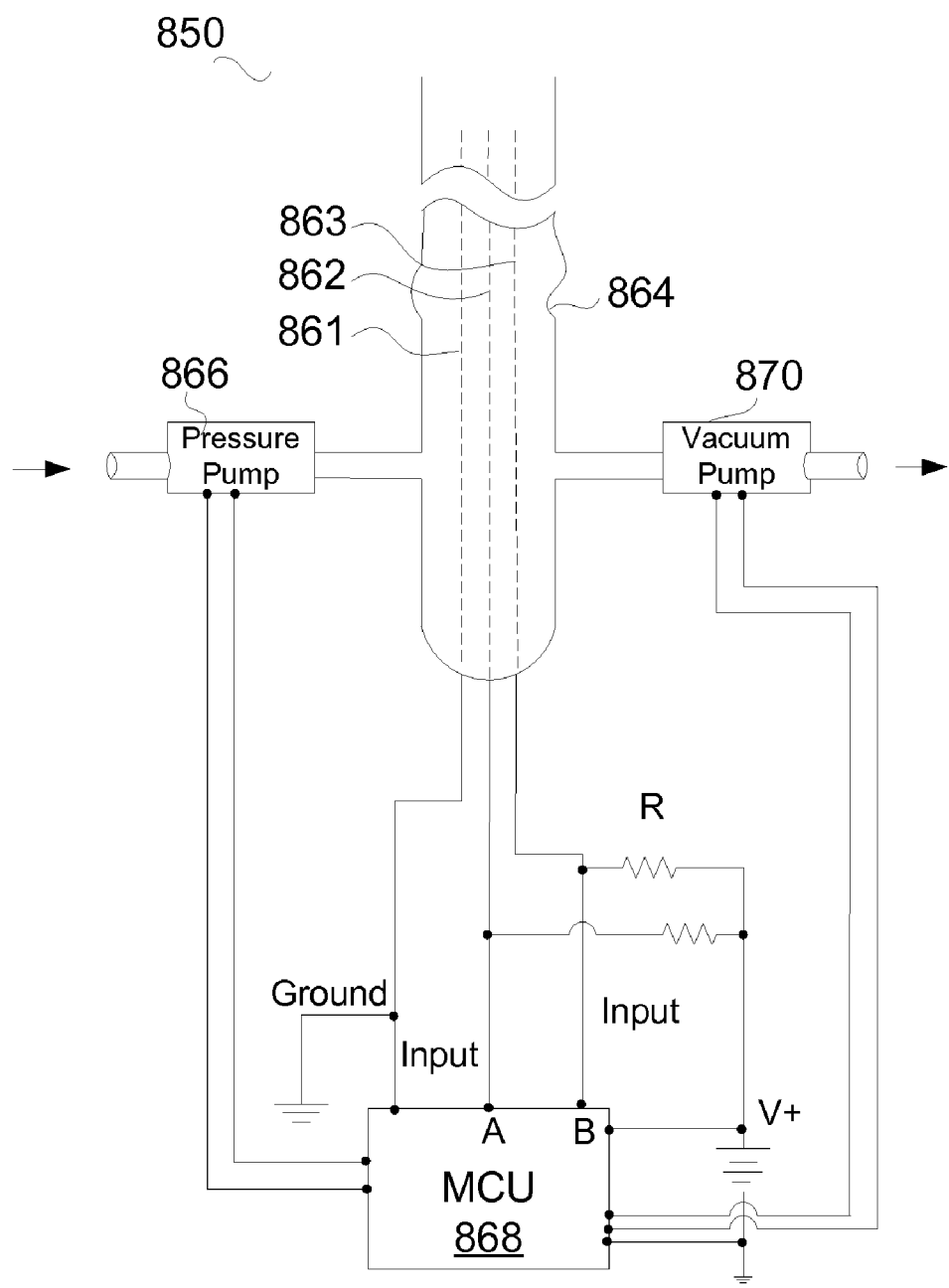
Figure 15C:
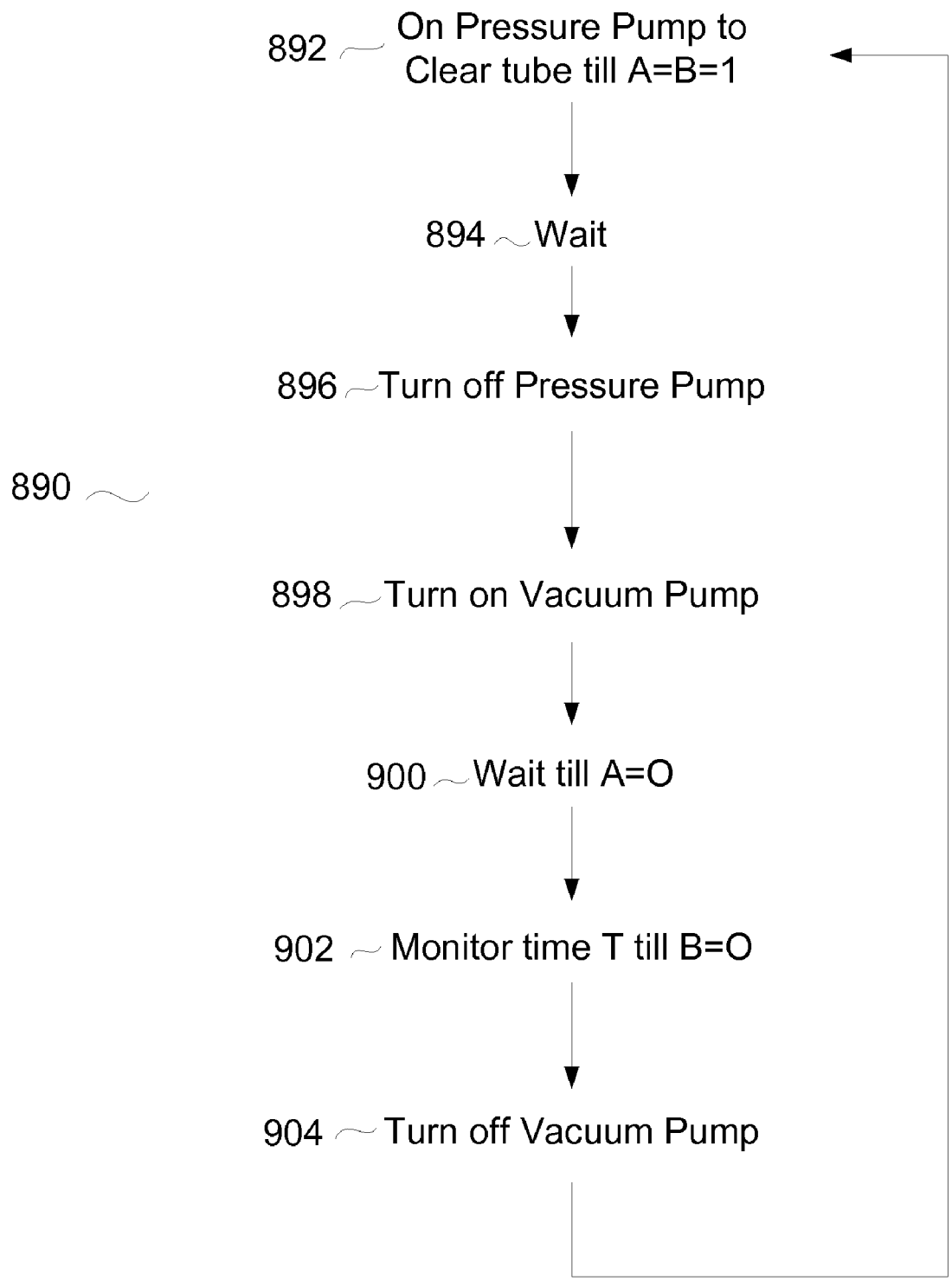

FIGS. 15A-C show a saliva sensor 850 that can continually measure certain attribute(s) in saliva according to different embodiments. FIG. 15A shows a sensor head 852 of the saliva sensor 850 inside the mouth, below the tongue in the saliva of the user. The sensor head 852 includes a hollow tube 854 with a small diameter. Because the tube's inner diameter is small, fluid can go up the tube based on capillary action. In one example, the tube has an inner diameter of 1 millimeter. The sensor head 852 includes three metal contacts, 856, 858 and 860, that are spaced linearly apart up the tube 854. The first contact 856 is close to or at the opening of the tube 854. The second contact 858 is at a certain fixed distance from the first contact 856, and the third contact 860 is further up the tube 854. Each contact is connected to a conducting wire or a conductor up the tube as shown in FIG. 15A, such as the wire 861 connecting to the contact 856, wire 862 to contact 858, and wire 863 to contact 860. In one embodiment, for structural reason, the wall thickness of the tube increases further away from the opening of the tube. In FIG. 15A, the hollow tube 854 is connected through an air-tight joint to another hollow tube 864 that has a thicker wall.

FIG. 15B shows a number of electrical components according to one embodiment connected to the conducting wires extended from the three metal contacts. FIG. 15C shows a set of operations 890 according to one embodiment based on the electrical embodiments shown in FIGS. 15A-B. First, a pressure pump 866 is turned on 892 to push air through the tube to clear saliva from the tube 862. With the saliva cleared from the tube 862, the inputs A and B received by a microcontroller unit (MCU) 868 will read high or logic 1. At this instant, saliva is not in the tube so the resistances between both the first contact 856 and the second contact 858, and the second 858 and the third 860 contacts are high. By keeping the pressure pump on for a preset amount of time, the tube remains clear during that period. This amount of time depends on how regularly the MCU 868 takes measurements. After waiting 894 for this amount of time, the MCU 868 turns off 896 the pressure pump 866 and turns on 898 a vacuum pump 870. The MCU 868 then waits 900 till the reading in its input A becomes ground or logic 0. At this instant, the resistance between the first 856 and the second 858 contact, through the conducting wires 861 and 862, is low due to the saliva touching the contacts. Then the MCU 868 monitors 902 the amount of time "T" till its input B also becomes ground or logic 0. At this instant, the resistance between the second 858 and the third 860 contacts, through the wires 863 and 862, is low, again due to the saliva. Then the MCU 868 turns off 904 the vacuum pump 870. This time T is inversely proportional to the viscosity of the saliva, which depends on how well hydrated the user is. And the process can repeat.

Instead of using a pressure pump and a vacuum pump, in another embodiment, the user can blow into the tube 854 to clear the tube 854. The MCU can just keep measuring for the time T without the pumps.

In one embodiment, measurements can be based on multiple sensors sensing the user. For example, a saliva sensor and an activity sensor, such as a pedometer, can be coupled to a bottle. Based on both the saliva and the level of activity (or the lack of activity), the bottle can recommend appropriate fluid consumption for the user.

In one embodiment, the sensor can include a sensor in a point-of-care test. For example, the sensor is a blood tester, which can be a self-testing blood tester, such as for cholesterol test or hormone test. Another example of a sensor in a point-of-care test is a flu test sensor.

Figure 16A:
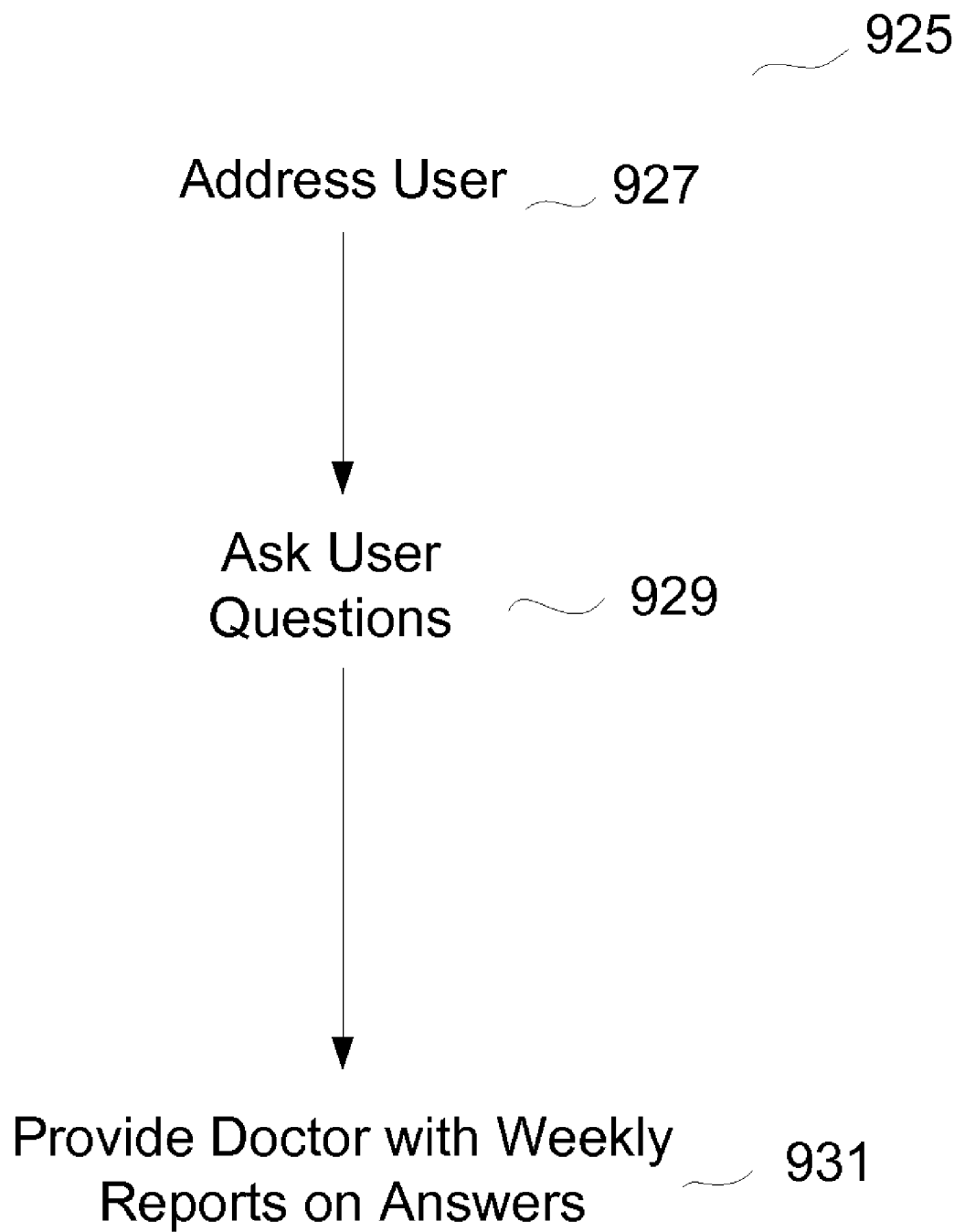

The substance in the bottle does not have to be limited to over-the-counter medication. In one embodiment, a bottle carries an antidepressant medication, such as Paroxetine or Fluoxetine. FIG. 16A shows a process 925 a bottle goes through according to one embodiment. After the bottle is activated, such as turned on each day, the bottle addresses 927 the user. Then the bottle asks 929 the user a number of questions. This can be based on a pull-down menu on a screen on the bottle. First, the bottle asks a question regarding the user's mood, and allows the user to select one out of a list of choices, such as very sad, sad, fed up, contented and happy. Then the bottle asks a question regarding the user's sleeping patterns, and allows the user to select one out of a list of choices, such as normal, not enough, and too much. The bottle can also ask the user a question regarding the user's activity level, and allows the user to select one out of a list of choices, such as cannot go to work, can go to work, function normally and function at 50% or less level. The bottle keeps track of the user's answers. Periodically, such as once a week, the bottle sends 931 the answers to the user's healthcare provider. The bottle can summarize the answers before sending to the provider. This can be done through a wired connection or wirelessly. Or, this can be done physically by the user visiting the health care provider with the bottle or with a memory device with information from the bottle. Based on the answers, the health care provider can adjust the future medication dosage accordingly, such as one pill a day, instead of two pills a day. The provider can also download the adjusted dosage to the bottle. Alternatively, instead of using a screen on the bottle to ask the user questions, the bottle can ask questions using audio (e.g., speech synthesis or pre-recorded audio).

In another embodiment, a bottle carries antihypertensive drugs. If the user has high blood pressure, both under and over dose can be dangerous to the user. The user can be a patient. In one embodiment, the user takes three different types of medication. They may include Diuretic, such as Hydrochlorthiazide, Ace Inhibitor, such as Captopril, and CA-Channel Inhibitor, such as Nifedipine. FIG. 16B shows a process 935 a bottle goes through according to one embodiment. When the user turns on the bottle, such as every day, the bottle addresses 937 the user, and suggests the user to measure his blood pressure. A blood pressure sensor can be coupled to the bottle, allowing the bottle to monitor 939 the measurements. If the measurements are beyond certain thresholds, such as systolic blood pressure above 180 or below 80, the bottle can provide alerts 941. This can be an alert to the user to go see a doctor immediately. In another example, a message is composed and then wirelessly sent to the user's healthcare provider. Data can be summarized and charted before sending. Blood pressure measurements can be plotted graphically or presented in diagrams. The data sent to the provider may include side effects of the medication(s). Using this data, the health care provider can adjust the medication(s) in a timely manner, which is typically faster than the usual patient report approach. Side effects can be monitored and found also.

In another embodiment, the user may get visual reports 943, such as a blood pressure graph on a display on the bottle. The graph can show his blood pressure being in a downward trend, presumably attributed to his effort of taking the recommended dosage of medication. Such reports can serve as an encouragement, motivating the user to continue to be diligent in taking the medication. However, if the trend is unfavorable, the user might be more inclined to consult his healthcare provider. Such constant monitoring can minimize side effects.

In one embodiment, the amount of medication in the bottle is monitored. If the user is not taking the medication as recommended, or if the medication is not re-filled, the user's health care provider and/or a family member of the user could be alerted. This can promote compliance of taking medication and also can potentially identify the user for further counseling or health professional visit.

In one embodiment, a base, such as one described in FIG. 11, is for one type of health issues. For example, a base is dedicated to hypertension, and there can be three selected areas for three bottles, one for each type of medications as described above.

Figure 16C:
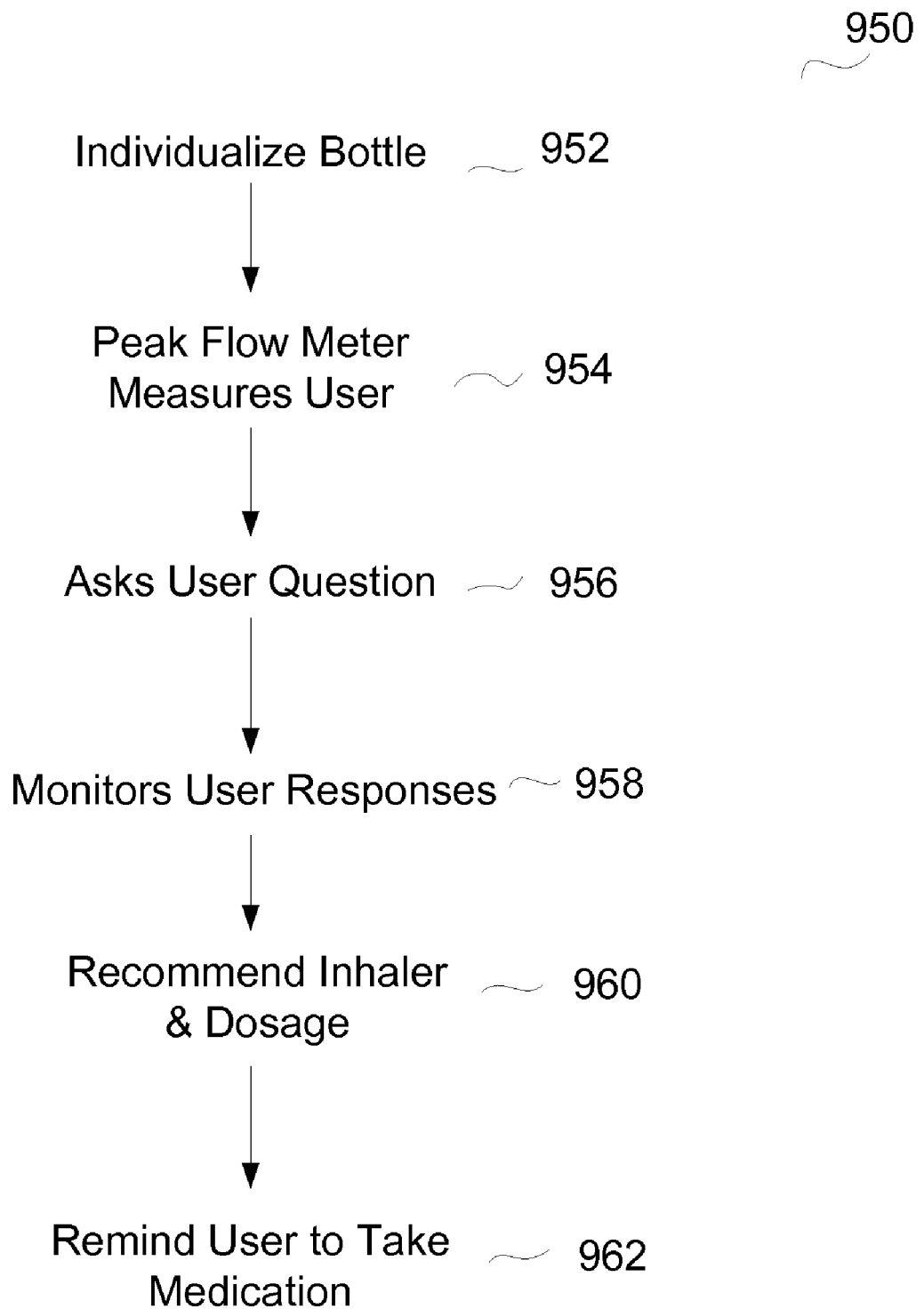

In one embodiment, the user has asthma. In this example, a bottle can include two metered dose inhalers, such as an Albuterol inhaler and a steroid inhaler, and the sensor includes a peak flow meter. FIG. 16C shows one process 950 the bottle goes through according to one embodiment. First, the bottle is individualized 952 based on the asthma condition of the user. Each user's peak flow number can be different. In one embodiment, the peak flow meter can be set into different zones, such as red, yellow and green zone. A health care professional can set the zone for the user based on the user's age, height and/or severity of asthma. In another embodiment, the bottle asks the user to enter his peak flow number. Every day, the peak flow meter takes readings 954 of the user. Then, the bottle asks 956 the user a number of questions regarding the user's symptoms. One question can be whether the user coughs or not. There can be a pull-down menu allowing the user to pick one of the three answers: often, occasionally and none. Another question can be whether the user wheezes or not. The bottle monitors 958 the user's responses.

Based on the measurements and answers to the questions, the bottle can recommend inhaler and dosage 960. For example, one recommendation can be related to the dosage of one type of inhalers for the day, which can include the number and frequency of the metered dose inhaler. For example, when the user's peak flow reading is at the red zone, the recommendation can be that the user should take two puffs of the Albuterol inhaler every 15 minutes for three times, then every four hours and alert the user to call his health care professional. As another example, when the user's peak flow reading is in the green zone, the recommendation can be that the user needs to take regular dose of inhaled steroid. When the user needs to take the medication, the bottle can automatically remind 962 the user, such as how many puffs the user needs to take.

Figure 16D:
Figure 16D:

In one embodiment, the user has attention deficit hyperactivity disorder. The medication can include Ritalin, Concerta, Adderall and/or Straterra. FIG. 16D shows one process 975 a bottle goes through according to one embodiment. Each day, the bottle asks 977 a guardian of the user, such as one of the user's parents, a number of questions regarding the user. For example, one question can be the user's attention scale. Another question can be the % of work the user finished that day. A third question can be the user's hyperactivity scale that day being high, medium or low. A fourth question can be the user's appetite being normal, eating too much, or eating too little. A fifth question can be whether the user has other side effects, such as dizzy, unable to sleep and palpitation. A sixth question could be the user's weight. The bottle may send summarized data, which can be charted and graphed, to the user's health care provider, so dose adjustment 979 of the medication can be ordered if necessary. This can help identify side effects quickly. In one embodiment, the bottle also includes a built-in safety mechanism because the medication typically can be a controlled substance. For example, the weight of the bottle is monitored. If the amount of medication is decreasing at a rate beyond, or more than a preset percentage beyond, the recommended usage, the doctor of the user can be alerted 981 because there might be drug abuse.

Different embodiments for other prescription drugs are also applicable to the present invention, such as Propanolol for migraine headache, insulin for diabetes, lipid lowering drugs, or other drugs that need to be taken regularly, such as daily, or other drugs where the user needs to be frequently monitored of side effects.

Different approaches on measuring the quantity of substance consumed or left in a bottle have been described. In one embodiment, the usage of the substance is measured or is deduced based on sensing the number of times the bottle or the cap of the bottle has been opened. In another embodiment, the usage is measured based on sensing the empty space in the bottle, such as the distance or the volume between the bottle cap and the top level of the substance, such as the fluid, in the bottle. The cap covers an opening of the bottle to keep the substance in the bottle. This can be done, for example, by measuring the time it takes for an ultra-sonic pulse to travel from the cap to the top level of the fluid and back. Based on the travel time, the distance is calculated. In yet another embodiment, the volume of the empty space is calculated based on measuring the acoustic resonance of the space to determine the size of the empty chamber.

Different types of inputs provided by the user have been described to provide user information. In one embodiment, another type of user inputs is for measuring the mental capacity of the user. For example, questions are presented to the user for answers. The questions can be mathematics questions. In another embodiment, the prior health history of the user, which can be provided by the user, can include the health history of one or more family members of the user.

Different types of instruments have been described that can be coupled to a bottle. In one embodiment, an exercise machine, such as a bicycle, a treadmill, or a stepper machine, is electrically coupled to the bottle. In another embodiment, a scale for measuring the weight of the user is coupled to a bottle. Information from such a machine, like a scale, can be sent to the bottle. Such information can be used together with other information in the bottle to provide, for example, recommendation to the user.

Different types of sensors have been described to measure the user.

In one embodiment, a bottle has additional information from one or more sensors measuring the environment in the immediate vicinity of the bottle. Examples of such sensors include one or more sensors for temperature, humidity, altitude, sunlight and/or ultra-violet radiation. In one embodiment, information regarding the environment can be used to dynamically determine whether the substance (e.g. medicine) in the bottle is still suitable for use by the user. The environment can also influence how often the substance is to be used by the user. In another embodiment, such information can be used together with other information in the bottle to provide, for example, recommendations for the user.

Different types of applications by a bottle have been described. In one embodiment, a bottle can provide personalized education and/or recommendation to the user regarding the substance the bottle contains. In one embodiment, the education and/or recommendation provided to the user is personalized to the user. For example, if the bottle carries antipyretic/analgesic medication, the appropriate amount recommended for a user can be tailored to the user based on the user's age, sex and weight. As another example, since many people with diabetes develop foot problem, though the bottle carries diabetes medication, the bottle provides education to the user regarding foot problem.

In another embodiment regarding applications, a bottle can recommend a user regarding a health program the user is involved. The bottle tracks the user's progress and compares the goals set by the user. Then, based on, for example, the user's consumption of the substance in the bottle, the user's weight and the user's activities, the bottle can determine if the program is effective, such as whether the user's weight-loss program is working.

Figure 17:
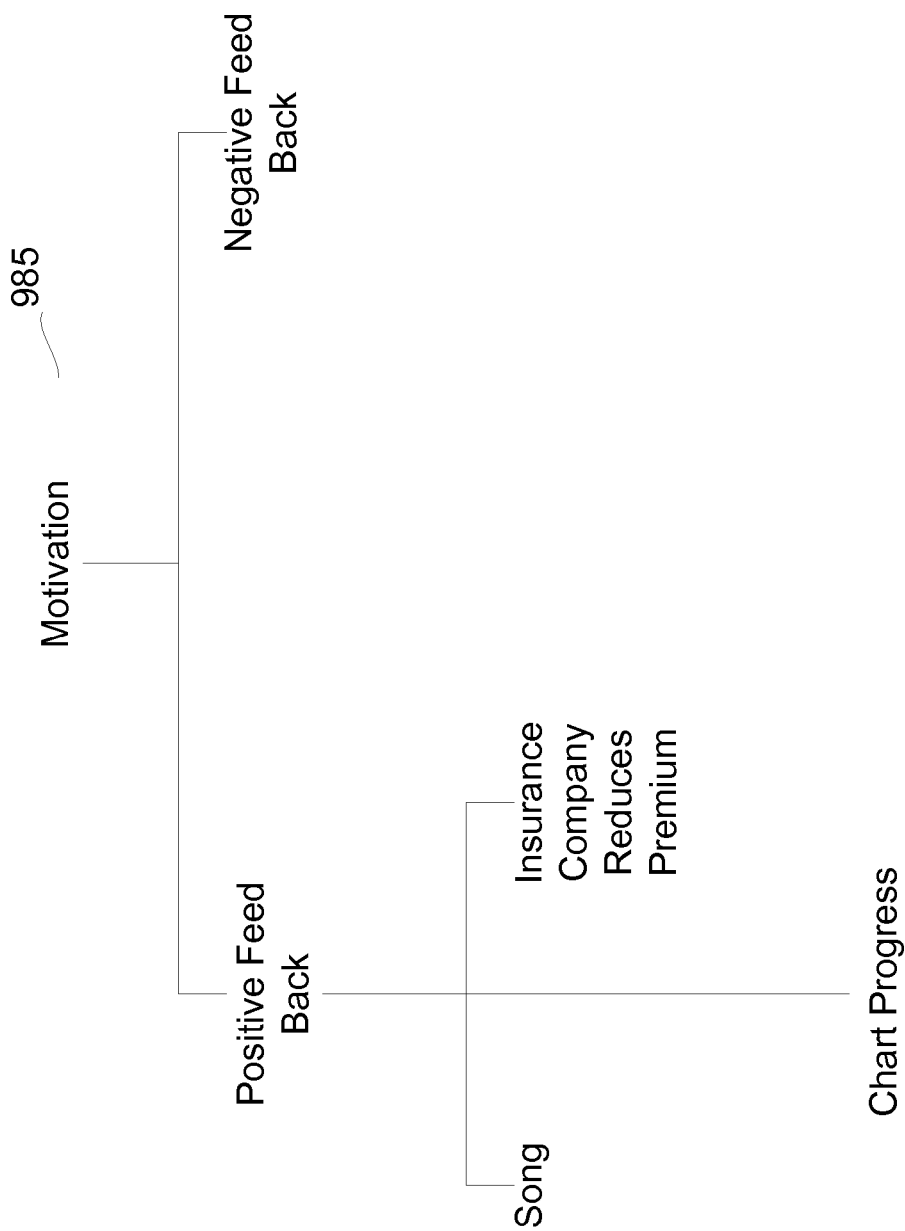
FIG. 17 shows examples of motivations provided to a user according to different embodiments of the invention.

In one embodiment, a bottle can provide motivation to the user. FIG. 17 shows a number of examples 985 of such motivations. This can be particularly helpful for substances, such as medications, that have to be taken regularly, such as daily. It is not uncommon for users to forget or simply ignore taking the substances. In some situations, such lack of discipline can be dangerous, such as for medication to reduce high blood pressure. In one approach, the bottle can provide positive feedbacks to the user who has followed the recommended consumption or prescription. Such positive feedbacks can be a song the user likes. In another approach, the bottle can chart the user's progress. For example, the user has regularly followed the suggested guidelines by his health care provider and his blood pressure is going down. The bottle can visually provide such a chart to the user, showing the period that the user has followed the guidelines and the user's blood pressure during the same period. In yet another embodiment, the user's insurance company reduces the user's premium if the user has regularly followed the suggested guidelines. Instead of positive feedback, in one embodiment, a bottle can provide the user with negative feedbacks if the user has not been following the suggested guidelines. A number of the negative feedbacks can be the opposites of the positive feedbacks just described. For example, instead of lowering the premium, the insurance company raises the premium if the user has not been following the guidelines.

In one embodiment, at least some of the functions previously described as performed by a bottle can be performed by another device. In another embodiment, a number of the functions previously described as performed by a bottle are performed by a computer coupled to a bottle, through, for example, a connector at the bottle. In a further embodiment, a number of functions previously described as performed by a bottle are performed by a remote website, wired or wirelessly coupled to a bottle. In yet another embodiment, a number of functions previously described as performed by a bottle are performed by a sensor electrically coupled to a bottle. Further, in one embodiment, at least some of the functions previously described as being performed by a bottle can be performed by a base, such as the base shown in FIG. 11. The base can be electrically coupled to the bottle.

Different embodiments have been described regarding a bottle carrying a substance. The substance can be in solid (such as pills), liquid or gaseous form, depending on the embodiment.

A number of embodiments have been described regarding a base coupled to a bottle. In one embodiment, a base can be used to measure the consumption of a substance in a container. One can scan the barcode on the container to download information regarding the substance into the base. The user can then weigh the container after the user consumes the substance, or can weigh before and after the consumption. This can allow the base to keep track of when and how much the user has consumed the substance.

A number of embodiments have been described based on a bottle. In one embodiment, instead of a bottle, different embodiments previously described are incorporated in a container, such as a box, a bag or a canister.

The various embodiments, implementations and features of the invention noted above can be combined in various ways or used separately. Those skilled in the art will understand from the description that the invention can be equally applied to or used in other various different settings with respect to various combinations, embodiments, implementations or features provided in the description herein.

A number of embodiments in the invention can be implemented in software, hardware or a combination of hardware and software. A number of embodiments of the invention can also be embodied as computer readable code on a computer readable medium. The computer readable medium is any data storage device that can store data which can thereafter be read by a computer system. Examples of the computer readable medium include read-only memory, random-access memory, CD-ROMs, magnetic tape, optical data storage devices, and carrier waves. The computer readable medium can also be distributed over network-coupled computer systems so that the computer readable code is stored and executed in a distributed fashion.

Numerous specific details are set forth in order to provide a thorough understanding of the present invention. However, it will become obvious to those skilled in the art that the invention may be practiced without these specific details. The description and representation herein are the common meanings used by those experienced or skilled in the art to most effectively convey the substance of their work to others skilled in the art. In other instances, well-known methods, procedures, components, and circuitry have not been described in detail to avoid unnecessarily obscuring aspects of the present invention.

Also, in this specification, reference to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments mutually exclusive of other embodiments. Further, the order of blocks in process flowcharts or diagrams representing one or more embodiments of the invention do not inherently indicate any particular order nor imply any limitations in the invention.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

The invention claimed is:

1. A health-related system for a user comprising:
a health-related base,
wherein the base comprises:
a first area configured to receive a receding area at the bottom of a bottle, the bottle being configured to carry a health related substance to be consumed by the user;
a detector configured to electronically detect information from the bottle;
a voice input mechanism allowing the user to provide an input directly entered into the base via voice;
a voice output device configured to allow the user to receive output from the base via voice;
a sensor configured to measure an attribute of the environment of the system;
a storage medium configured to electrically store a piece of information regarding the user; and
an electrical connecting mechanism configured to receive an electrical connecting mechanism at the bottle so that information from the bottle is configured to be accessed by the base,
wherein at least based on the sensor measurement, the base is configured to determine if the health related substance is still suitable to be consumed,
wherein the base, via the voice output device, is configured to ask the user at least a question,
wherein the base, via the voice input mechanism, is configured to receive a voice input from the user to respond to the at least one question, and
wherein the base is further configured to provide electronic assistance regarding taking the health-related substance based on at least the voice input from the voice input mechanism.

2. The health-related system as recited in claim 1, wherein the base further comprises a space configured to receive a sensor configured to measure an attribute of the user, and wherein the base stores the sensor measurement and the time of the measurement.

3. The health-related system as recited in claim 2,
wherein the voice input is also time stamped, and
wherein the system links the sensor measurement and the time stamped voice input together for later retrieval.

4. The health-related system as recited in claim 2 wherein the base is configured to provide a recommendation regarding the dosage of the health-related substance for the user based on the sensor measurement of the attribute of the user.

5. The health-related system as recited in claim 2 wherein the base is configured to send information related to the measurement to a person or entity interested in the well being of the user.

6. The health-related system as recited in claim 1, wherein the system includes the bottle.

7. The health-related system as recited in claim 1 wherein the base is configured to understand natural language.

8. The health-related system as recited in claim 1 wherein the base also stores educational information regarding the health-related substance including its side effects, precautions, drug interactions, and/or health news related to the health-related substance.

9. The health-related system as recited in claim 8 wherein the educational information is personalized to the user.

10. The health-related system as recited in claim 1, wherein the electrical connecting mechanism of the base is configured to receive the electrical connecting mechanism at the bottle wirelessly.

11. The health-related system as recited in claim 1,
wherein the base is configured to ask the user a plurality of questions via the voice output device, and to receive a plurality of answers from the user corresponding to the plurality of questions via the voice input mechanism, and
wherein the base is configured to provide electronic assistance regarding taking the health-related substance based on at least the plurality of answers from the voice input mechanism.

12. The health-related system as recited in claim 1 wherein the base is configured to determine whether the user has followed an instruction regarding taking the health-related substance.

13. The health-related system as recited in claim 1 wherein the health-related substance is a controlled substance and the base is configured to determine if there is user abuse in taking the health-related substance.

14. The health-related system as recited in claim 1,
wherein the base is configured to store information regarding the health-related substance being removed from the bottle, and
wherein the base is configured to send information regarding the health-related substance being removed from the bottle to a person or entity interested in the well being of the user.

15. The health-related system as recited in claim 1 wherein the base includes electronics configured to provide motivation to the user to consume the health related substance.

16. The health-related system as recited in claim 15, wherein the motivation is related to health insurance of the user.

17. The health-related system as recited in claim 1 wherein the base is configured to provide a reminder for the user to take the health-related substance via the voice output device.

18. A health-related base comprising:
a first area configured to receive a second area at the bottom of a bottle that is configured to carry a health related substance to be consumed by a user from an opening at the bottle;
a detector configured to electronically detect information from the bottle;
a physical entry input mechanism allowing the user to provide an input directly entered into the base via physical entry;
a sensor configured to measure an attribute of the environment of the system;

an output device configured to allow the user to receive output from the base; and an electrical connecting mechanism at the first area configured to receive an electrical connecting mechanism at the second area of the bottle so that information from the bottle is configured to be accessed by the base and information from the base is able to be transmitted for receiving by electronics in the bottle via the connecting mechanisms, wherein at least based on the sensor measurement, the base is configured to determine if the health related substance is still suitable to be consumed, wherein the base includes electronics configured to provide motivation to the user that is emotional in nature, or that is related to health insurance of the user, to consume the health related substance, and wherein the base is further configured to provide electronic assistance regarding taking the health-related substance.

19. The health-related base as recited in claim 18 wherein the motivation is a song.

20. The health-related base as recited in claim 18 wherein the first area includes a protruding area.

21. A health-related base comprising:

a first area configured to receive a second area at the bottom of a bottle that is configured to carry a health related substance to be consumed by a user from an opening in the vicinity at the top of the bottle;

a detector configured to electronically detect information from the bottle;

a physical entry input mechanism allowing the user to provide an input directly entered into the base via physical entry;

an output device configured to allow the user to receive output from the base;

a sensor configured to sense an attribute of the environment of the base; and an electrical connecting mechanism at the first area configured to receive an electrical connecting mechanism at the second area of the bottle so that information from the bottle is configured to be accessed by the base and information from the base is able to be transmitted for receiving by electronics in the bottle through the electrical connection, wherein at least based on a measurement by the sensor, the base is configured to determine if the health related substance is still suitable to be consumed.

22. The health-related base as recited in claim 21, wherein the physical entry input mechanism includes a voice input mechanism that allows the user to provide an input directly entered into the base via voice, wherein the output device includes a voice output device that allows the user to receive output from the base via voice, wherein via the voice output device, the base is configured to ask the user at least a question, wherein via the voice input mechanism, the base is configured to receive a voice input from the user responding to the at least a question, and wherein the base is configured to provide electronic assistance regarding taking the health-related substance based on at least the voice input from the voice input mechanism.

23. The health-related base as recited in claim 21, wherein the first area includes a protruding area, and wherein the electrical connecting mechanism at the first area is a physical electrical connector configured to receive and to mechanically secure to the electrical connecting mechanism at the second area of the bottle.

* * * * *